(12) United States Patent
Kilali et al.

(10) Patent No.: US 10,684,202 B2
(45) Date of Patent: Jun. 16, 2020

(54) APPARATUS AND METHODS OF MECHANICAL TESTING MATERIALS

(71) Applicant: Corning Incorporated, Corning, NY (US)

(72) Inventors: Yassine Kilali, Nogent sur Seine (FR); Khaled Layouni, Painted Post, NY (US)

(73) Assignee: Corning Incorporated, Corning, NY (US)

(*) Notice: Subject to any disclaimer, the term of this patent is extended or adjusted under 35 U.S.C. 154(b) by 32 days.

(21) Appl. No.: 15/765,833

(22) PCT Filed: Oct. 5, 2016

(86) PCT No.: PCT/US2016/055465
§ 371 (c)(1),
(2) Date: Apr. 4, 2018

(87) PCT Pub. No.: WO2017/062433
PCT Pub. Date: Apr. 13, 2017

(65) Prior Publication Data
US 2019/0113425 A1    Apr. 18, 2019

Related U.S. Application Data

(60) Provisional application No. 62/237,879, filed on Oct. 6, 2015.

(51) Int. Cl.
*G01N 3/02*     (2006.01)
*G01N 3/08*     (2006.01)
*G01N 33/38*    (2006.01)

(52) U.S. Cl.
CPC ............... *G01N 3/02* (2013.01); *G01N 3/08* (2013.01); *G01N 33/388* (2013.01);
(Continued)

(58) Field of Classification Search
CPC .......... G01N 3/02; G01N 3/08; G01N 33/388; G01N 2203/0452; G01N 2203/0266; G01N 2203/0062; G01N 2203/0286
See application file for complete search history.

(56) References Cited

U.S. PATENT DOCUMENTS 4,534,225 A    8/1985   Peacock et al.
7,309,520 B2   12/2007  Kosack et al.
(Continued)

FOREIGN PATENT DOCUMENTS

WO    1994028388 A1    12/1994
WO    2009095828 A2    8/2009

OTHER PUBLICATIONS

ASTM for Monotonic Compressive Strength of Advanced Ceramics At Ambient Temperature; Designation C1424-10; 2014; 13 Pages.
(Continued)

*Primary Examiner* — Jonathan M Dunlap
(74) *Attorney, Agent, or Firm* — Kurt R. Denniston

(57) ABSTRACT

An apparatus and method to strength test porous ceramic honeycomb bodies. The apparatus includes an interlayer between at least one platen and a surface of the high porosity honeycomb body to be tested. The method includes disposing at least one interlayer between at least one platen and an end face of the body, applying a force to the high porosity ceramic honeycomb body and monitoring a result of applying the force. The interlayer comprises a surface weight of about 350 g/m² and a thickness in a direction N between facing surfaces load platens of at least about 20 mm. Axial and radial localized stamping tests also strength test porous ceramic honeycomb bodies.

20 Claims, 29 Drawing Sheets

(52) U.S. Cl.
CPC ............... *G01N 2203/0062* (2013.01); *G01N 2203/0266* (2013.01); *G01N 2203/0286* (2013.01); *G01N 2203/0452* (2013.01)

(56) References Cited

U.S. PATENT DOCUMENTS

| | | | |
|---|---|---|---|
| 7,415,890 B2* | 8/2008 | Workman | B32B 5/18 |
| | | | 73/818 |
| 9,182,330 B2* | 11/2015 | Kismarton | G01M 5/0091 |
| 9,239,236 B2* | 1/2016 | Griess | G01M 5/0091 |
| 2004/0007077 A1 | 1/2004 | Hijikata | |
| 2004/0079167 A1 | 4/2004 | Boyko et al. | |
| 2004/0249304 A1 | 12/2004 | Earthman et al. | |
| 2005/0106379 A1 | 5/2005 | Workman | |
| 2005/0107244 A1* | 5/2005 | Ichikawa | B01D 53/885 |
| | | | 502/60 |
| 2008/0237428 A1 | 10/2008 | Kobayashi et al. | |
| 2012/0092809 A1* | 4/2012 | Tamachi | H01G 9/155 |
| | | | 361/502 |
| 2015/0020603 A1* | 1/2015 | Kismarton | G01M 5/0091 |
| | | | 73/800 |
| 2015/0233709 A1 | 8/2015 | Griess et al. | |

OTHER PUBLICATIONS

Awaji et al; "Compressive Testing of Ceramics", Ceramics International 20 (1994) p. 159-167.
Freudenberg Innovating Together; Filtration Technologies; p. 15 Series Filter Mats; Downloaded Aug. 13, 2018; 3 Pages; https://products.freudenberg-filter.com/en/p/products/filter-mats/filter-mats/p-15-series.
Freudenberg Innovating Together; Filtration Technologies; PSB Series Filter Mats; 3 Pages; Downloaded Aug. 13, 2018; https://products.freudenberg-filter.com/en/p/products/filter-mats/filter-mats/psb-series.
International Search Report and Written Opinion of the International Searching Authority; PCT/US2016/055465 dated May 30, 2017; 21 Pages; European Patent Office.
Invitation to Pay Additional Fees of the International Searching Authority; PCT/US2016/055465; dated Jan. 20, 2017; 7 Pages; European Patent Office.

* cited by examiner

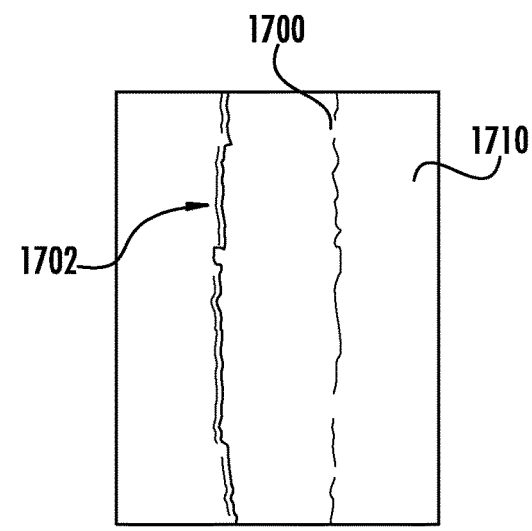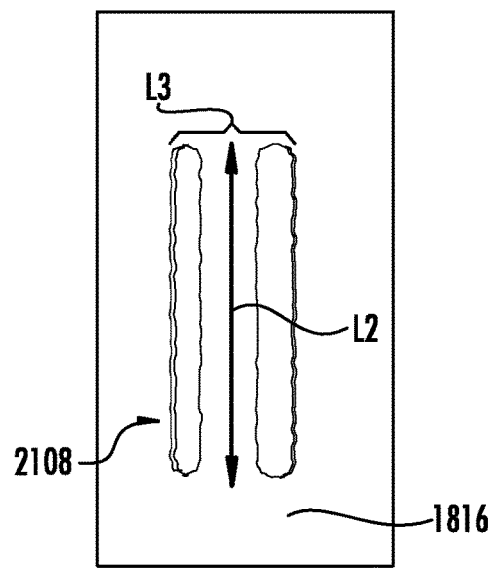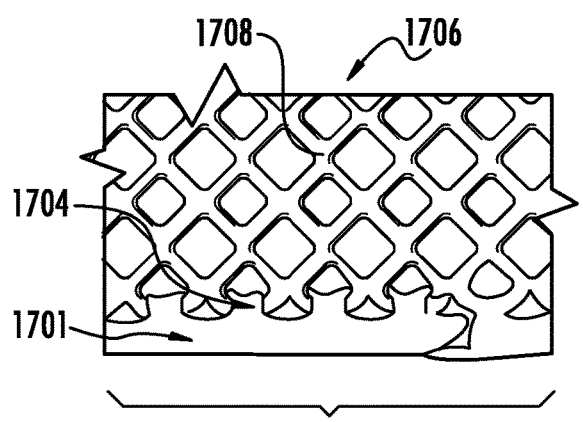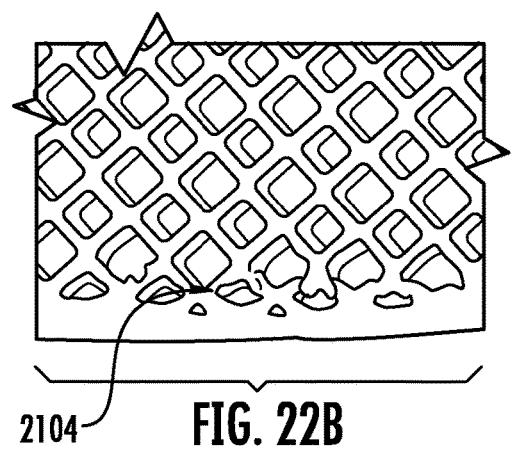
FIG. 22A
FIG. 22B

APPARATUS AND METHODS OF MECHANICAL TESTING MATERIALS

CROSS-REFERENCE TO RELATED APPLICATIONS

This application is a national stage application under 35 U.S.C. § 371 of International Patent Application Serial No. PCT/US2016/055465, filed on Oct. 5, 2016, which claims the benefit of priority of U.S. Provisional Application Ser. No. 62/237,879 filed on Oct. 6, 2015, the contents of both are relied upon and incorporated herein by reference in their entireties.

BACKGROUND

Field

Exemplary embodiments of the present disclosure relate to apparatus and methods of mechanical testing materials, more particularly, to apparatus and methods having an improved layer for strength testing of high porosity ceramic honeycomb bodies.

Discussion of the Background

After-treatment of exhaust gas from internal combustion engines may use catalysts supported on high-surface area substrates and, in the case of diesel engines and some gasoline direct injection engines, a catalyzed or non-catalyzed filter for the removal of carbon soot particles. Porous ceramic flow-through honeycomb substrates and wall-flow honeycomb filters may be used in these applications.

The above information disclosed in this Background section is only for enhancement of understanding of the background of the disclosure and therefore it may contain information that does not form any part of the prior art nor what the prior art may suggest to a person of ordinary skill in the art.

SUMMARY

Exemplary embodiments of the present disclosure provide a mechanical testing apparatus to test the mechanical behavior of materials.

Exemplary embodiments of the present disclosure also provide a mechanical testing apparatus to test the strength of high porosity ceramic honeycomb bodies.

Exemplary embodiments of the present disclosure also provide a method of testing the mechanical behavior of materials.

Exemplary embodiments of the present disclosure also provide a method of testing the strength of high porosity ceramic honeycomb bodies.

Additional features of the disclosure will be set forth in the description which follows, and in part will be apparent from the description, or may be learned by practice of the disclosure.

An exemplary embodiment discloses a mechanical testing apparatus to test the mechanical behavior of a specimen of material. The apparatus includes a first platen and a second platen comprising facing surfaces configured to apply a force to the specimen of material when disposed between the facing surfaces of the first platen and the second platen. The apparatus includes at least one intermediate platen configured to be disposed between at least one of the facing surface of the first platen and the specimen of material, and the facing surface of the second platen and the specimen of material, wherein the first platen and the second platen have a hardness greater than the at least one intermediate platen. The apparatus includes a controller configured to monitor a result when force is applied to the specimen disposed between the first platen and the second platen. The at least one intermediate platen comprises a surface weight of about 350 g/m$^2$ and a thickness in a direction N between the facing surfaces of the first platen and the second platen of at least about 20 mm.

An exemplary embodiment also discloses a mechanical testing apparatus to test the strength of a high porosity ceramic honeycomb body. The apparatus includes a first platen and a second platen comprising facing surfaces configured to apply a force to the high porosity ceramic honeycomb body when disposed between the facing surfaces of the first platen and the second platen. The apparatus includes at least one intermediate platen configured to be disposed between at least one of the facing surface of the first platen and the high porosity ceramic honeycomb body, and the facing surface of the second platen and the high porosity ceramic honeycomb body, wherein the first platen and the second platen have a hardness greater than the at least one intermediate platen. The apparatus includes a controller configured to monitor a result when force is applied to the high porosity ceramic honeycomb body disposed between the first platen and the second platen. The at least one intermediate platen comprises a surface weight of about 350 g/m$^2$ and a thickness in a direction N between the facing surfaces of the first platen and the second platen of at least about 20 mm.

An exemplary embodiment also discloses a method of testing the mechanical behavior of a material. The method includes disposing a specimen of the material between facing surfaces of a first platen and a second platen, a first end face of the specimen disposed toward the first platen and a second end face disposed toward the second platen. The method includes disposing at least one intermediate platen between at least one of the facing surface of the first platen and the specimen of the material, and the facing surface of the second platen and the specimen of the material, wherein the first platen and the second platen comprise a hardness greater than the at least one intermediate platen. The method includes applying a force to the specimen of the material between the first platen and the second platen via the facing surfaces of first platen and the second platen; and monitoring a result of applying the force. The at least one intermediate platen has a surface weight of about 350 g/m$^2$ and a thickness in a direction N between the facing surfaces of the first platen and the second platen of at least about 20 mm.

An exemplary embodiment also discloses a method of testing a high porosity ceramic honeycomb body. The method includes disposing a high porosity ceramic honeycomb body comprising channels defined by a plurality of intersecting porous walls that extend along the axis of the honeycomb body between a first end face and a second end face between facing surfaces of a first platen and a second platen, the first end face disposed toward the first platen and the second end face disposed toward the second platen. The method includes disposing at least one intermediate platen between at least one of the facing surface of the first platen and the first end face, and the facing surface of the second platen and the second end face, wherein the first platen and the second platen comprise a hardness greater than the at least one intermediate platen. The method includes applying a force to the high porosity ceramic honeycomb body between the first platen and the second platen via the facing surfaces of first platen and the second platen; and monitoring a result of applying the force. The at least one intermediate platen has a surface weight of about 350 g/m$^2$ and a thickness in a direction N between the facing surfaces of the first platen and the second platen of at least about 20 mm.

It is to be understood that both the foregoing general description and the following detailed description are exemplary and explanatory and are intended to provide further explanation of the disclosure.

BRIEF DESCRIPTION OF THE FIGURES

The accompanying drawings, which are included to provide a further understanding of the disclosure and are incorporated in and constitute a part of this specification, illustrate exemplary embodiments of the disclosure, and together with the description serve to explain the principles of the disclosure.

Figure 9A:
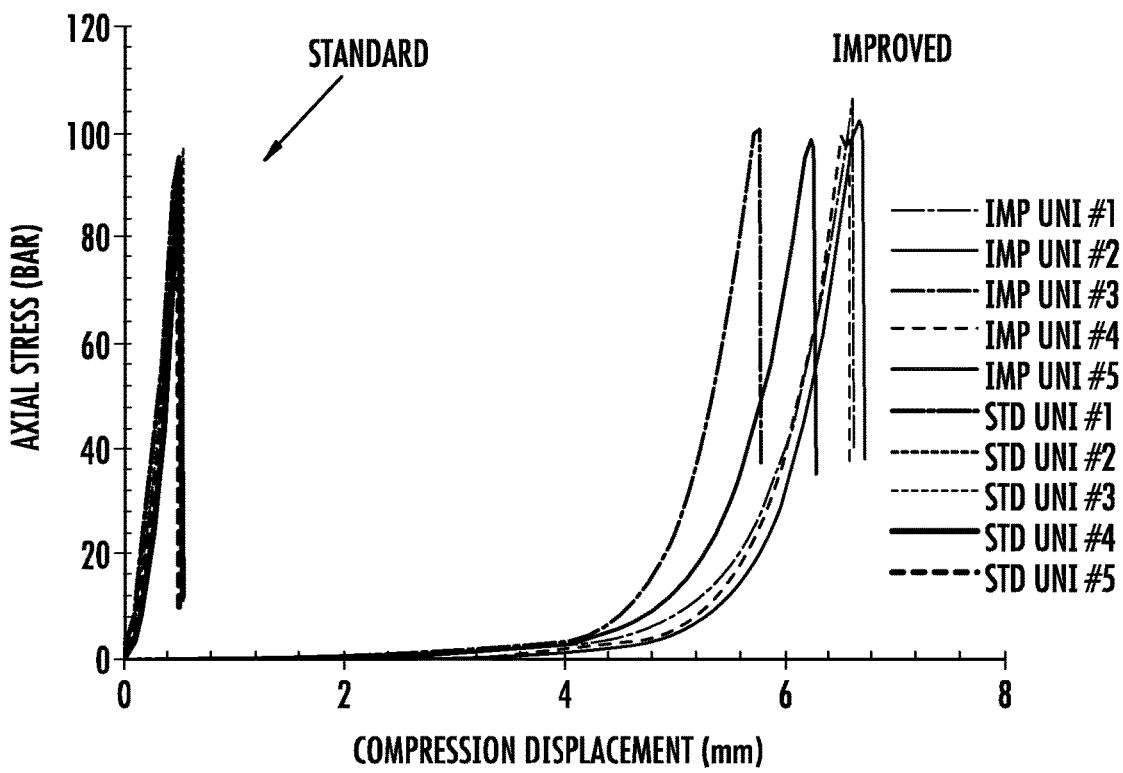
Figure 9B:
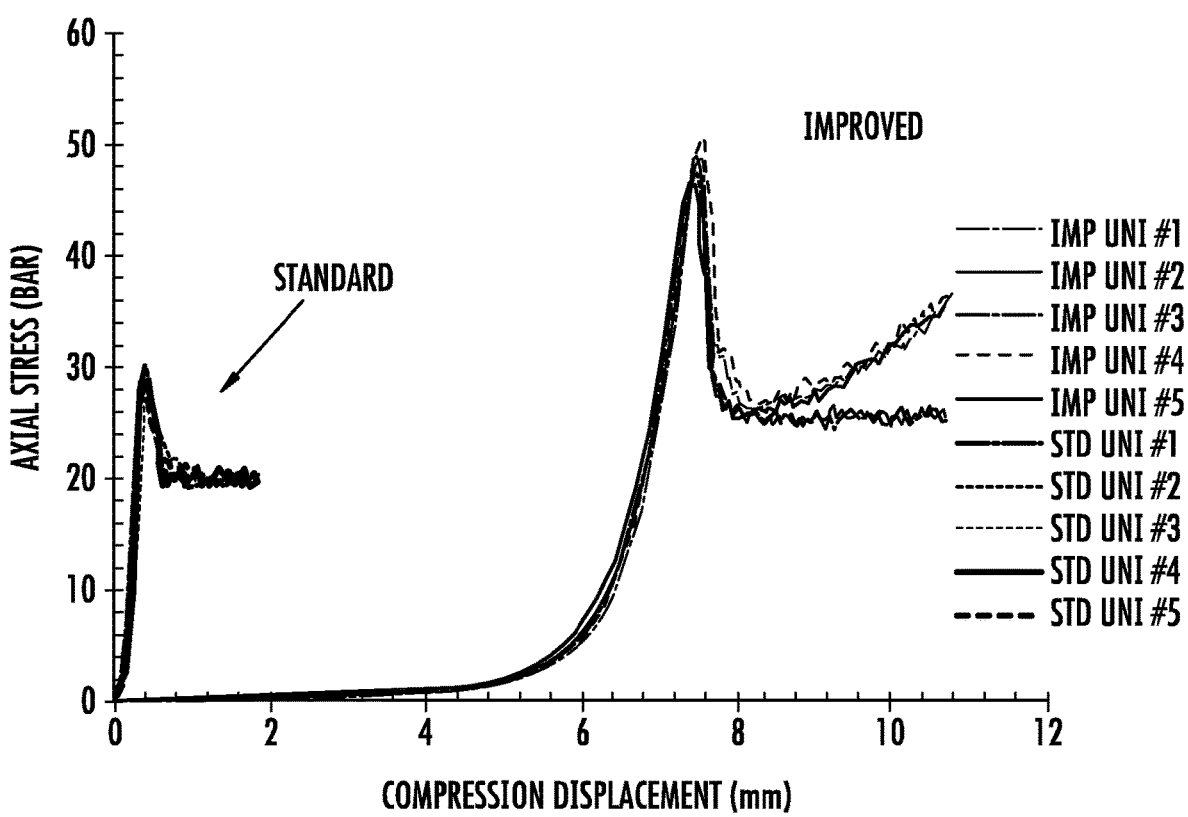

Comparative uniaxial A-axis strength results from a comparative mechanical apparatus set-up for compressive strength of a high porosity ceramic honeycomb body are presented in FIG. 9A and compared to improved interlayer A-axis strength results from a mechanical apparatus set-up for compressive strength of a high porosity ceramic honeycomb body according to exemplary embodiments of the disclosure as presented in FIG. 9B.

Figure 10A:
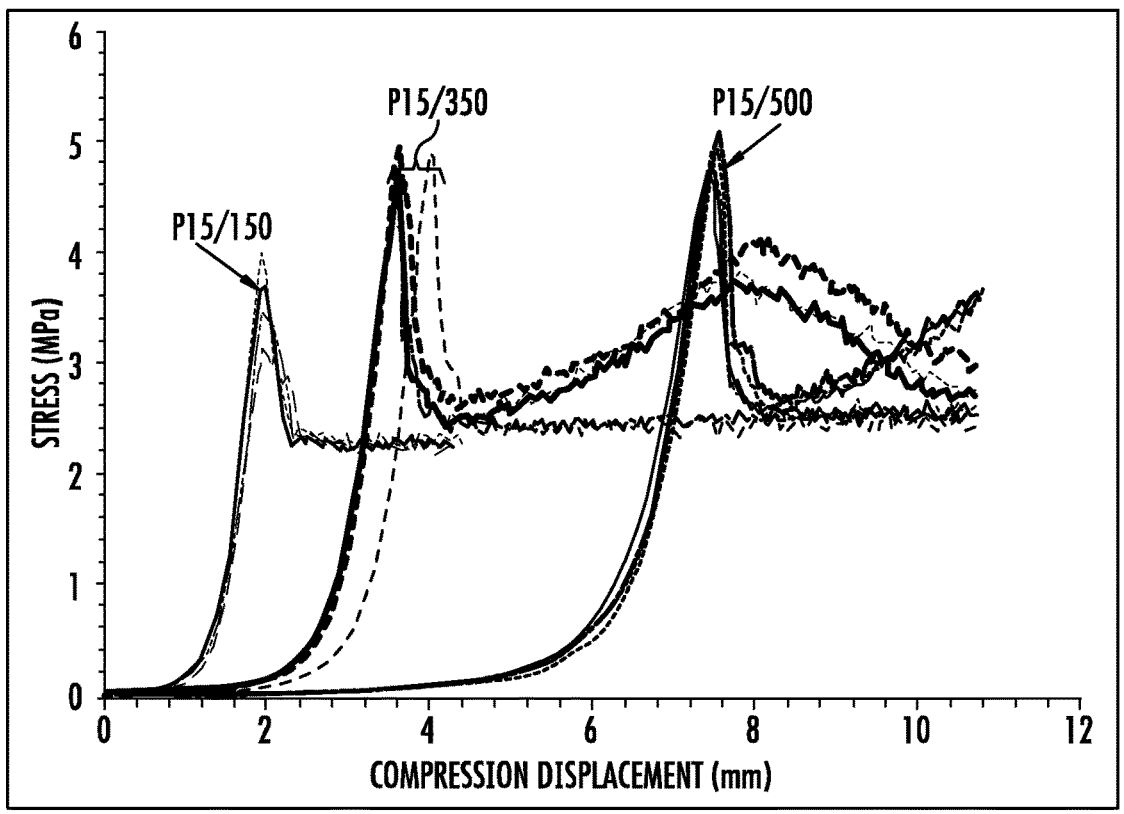
Figure 10B:
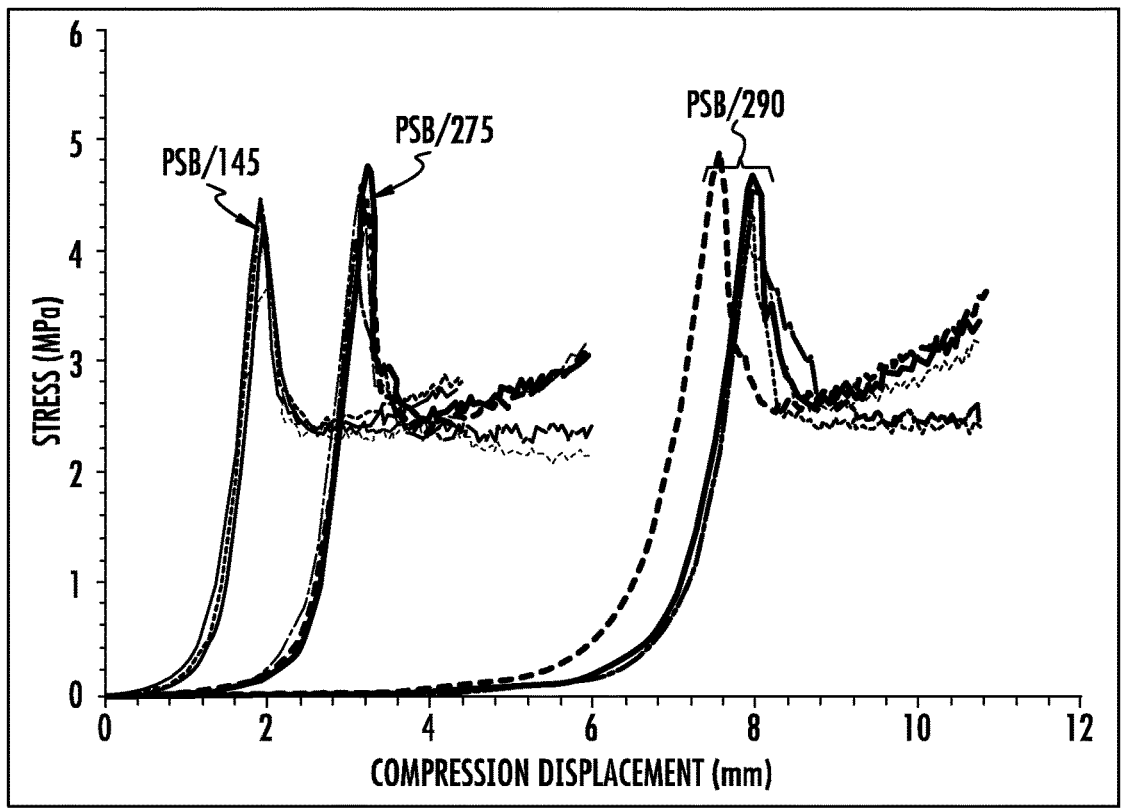
Figure 10C:
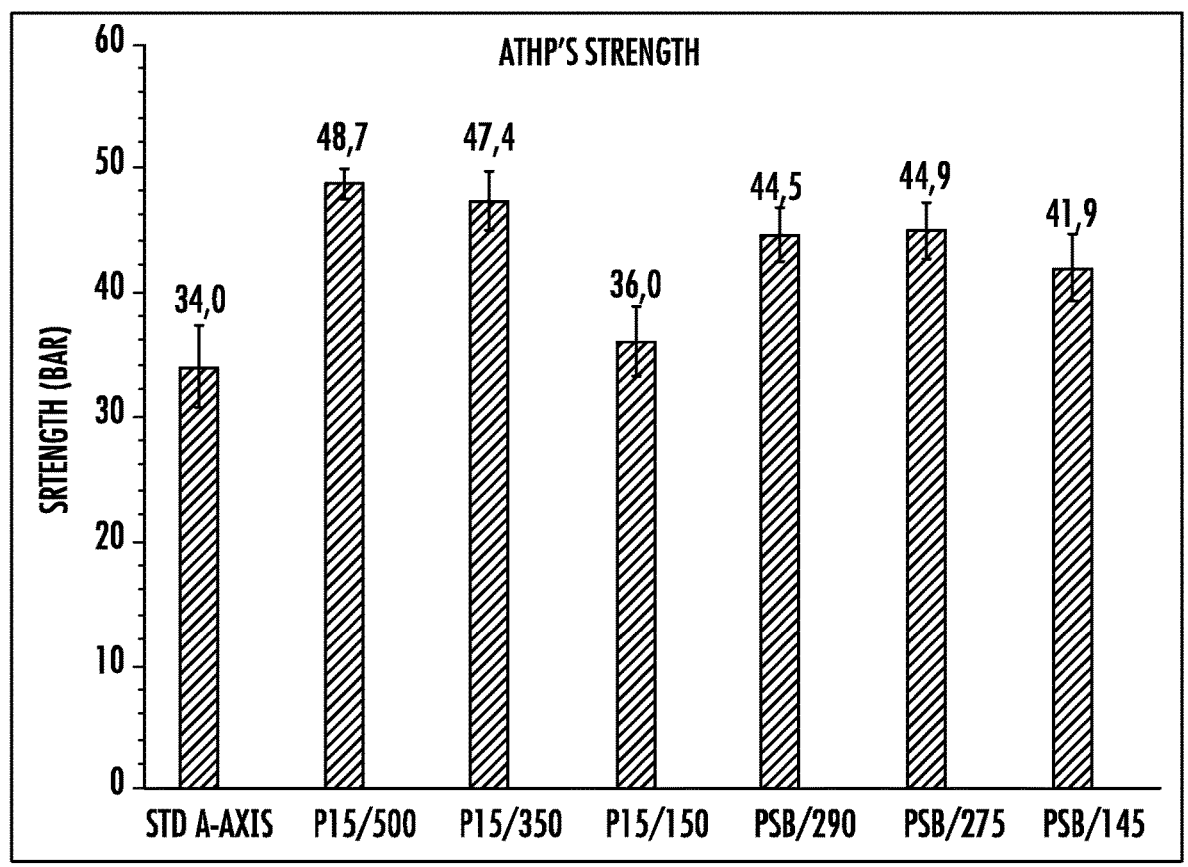

FIGS. 10A, 10B, and 10C present graphical plot of data showing the impact of mat properties in the interlayer on improved A-axis strength results for high porosity ceramic honeycomb bodies according to exemplary embodiments of the disclosure.

Figure 11:
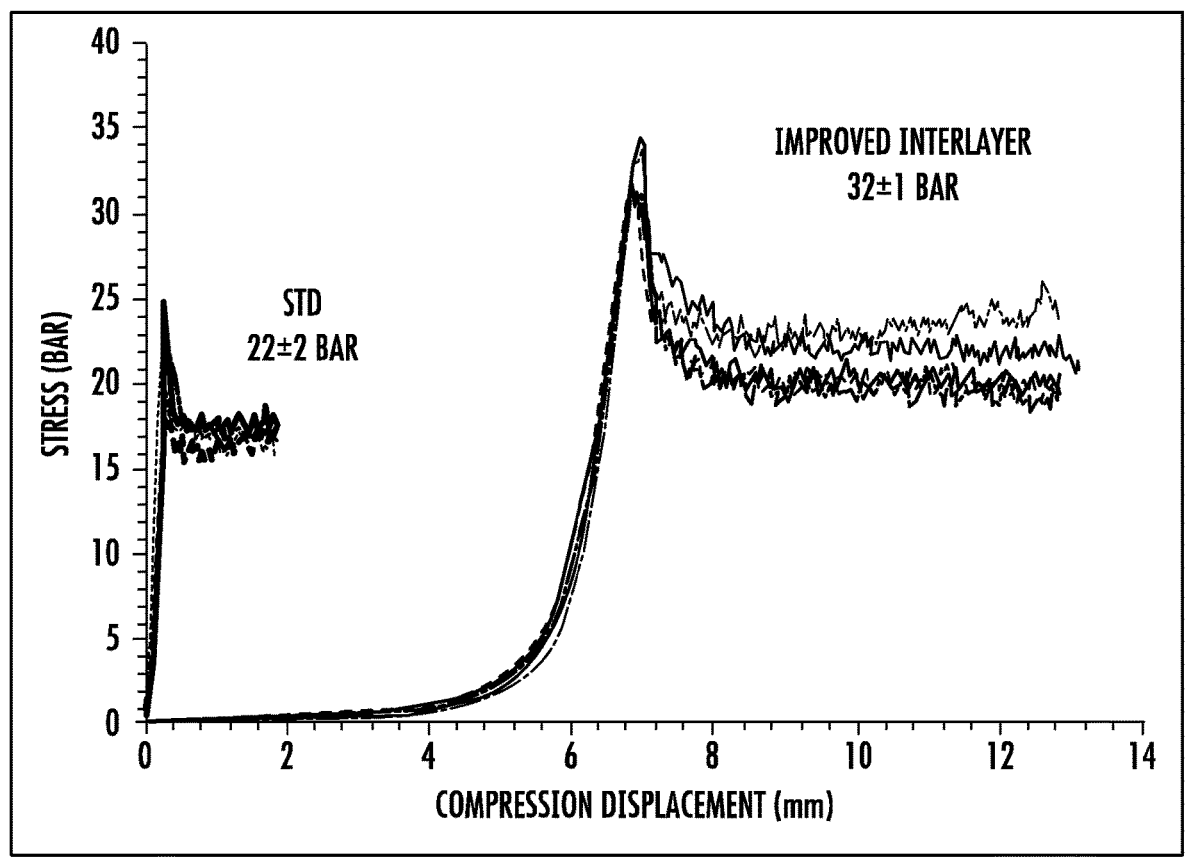

Comparative uniaxial A-axis strength results from a comparative mechanical apparatus set-up for compressive strength of a high porosity ceramic honeycomb body compared to improved interlayer A-axis strength results from a mechanical apparatus set-up for compressive strength of a high porosity ceramic honeycomb body according to exemplary embodiments of the disclosure are presented in FIG. 11.

Figure 12:
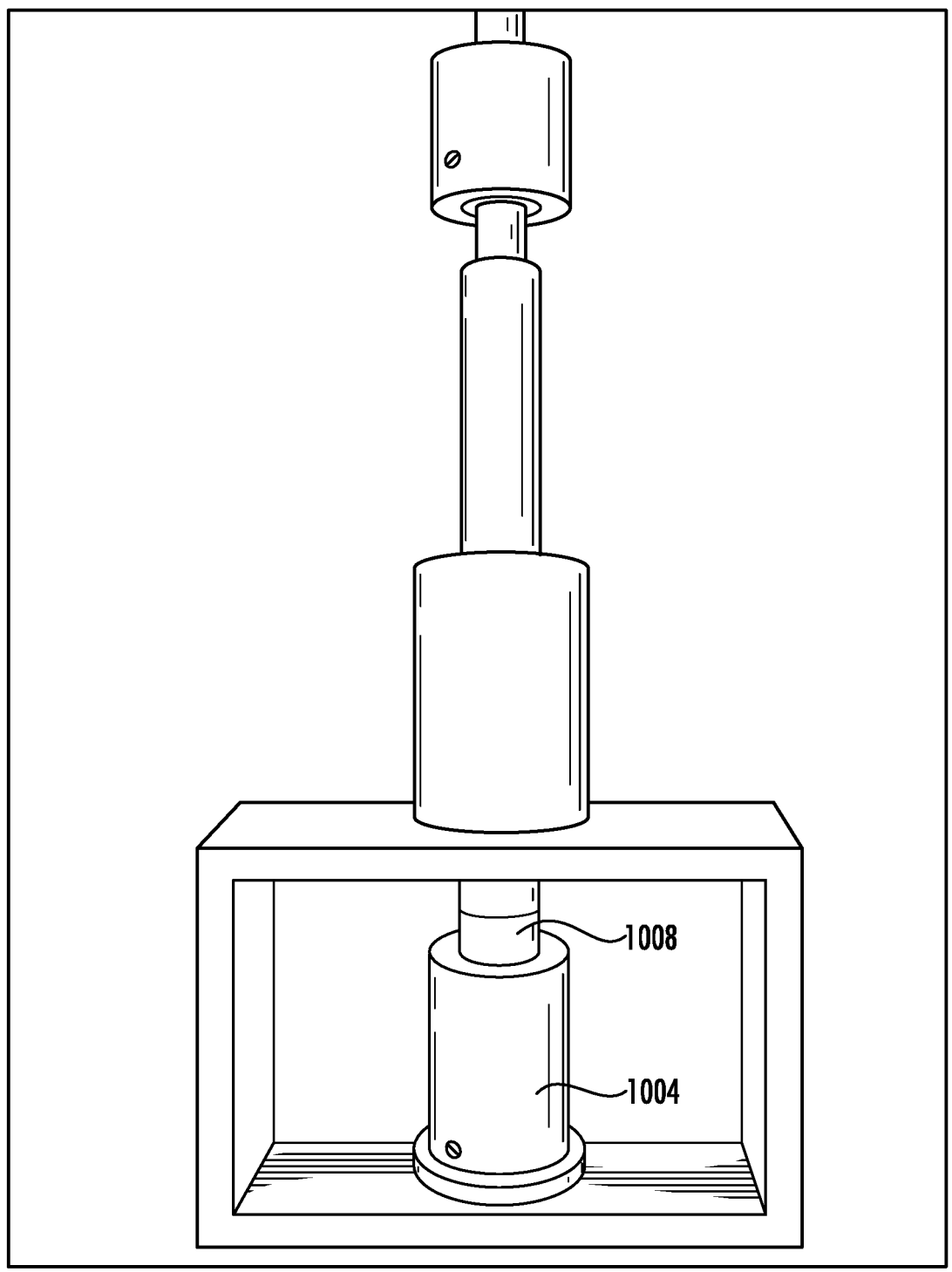

FIG. 12 shows an oedometric compression mechanical apparatus set-up for oedometric compressive strength of a high porosity ceramic honeycomb body which also showed improved strength results with the improved interlayer according to exemplary embodiments of the disclosure.

Figure 13:
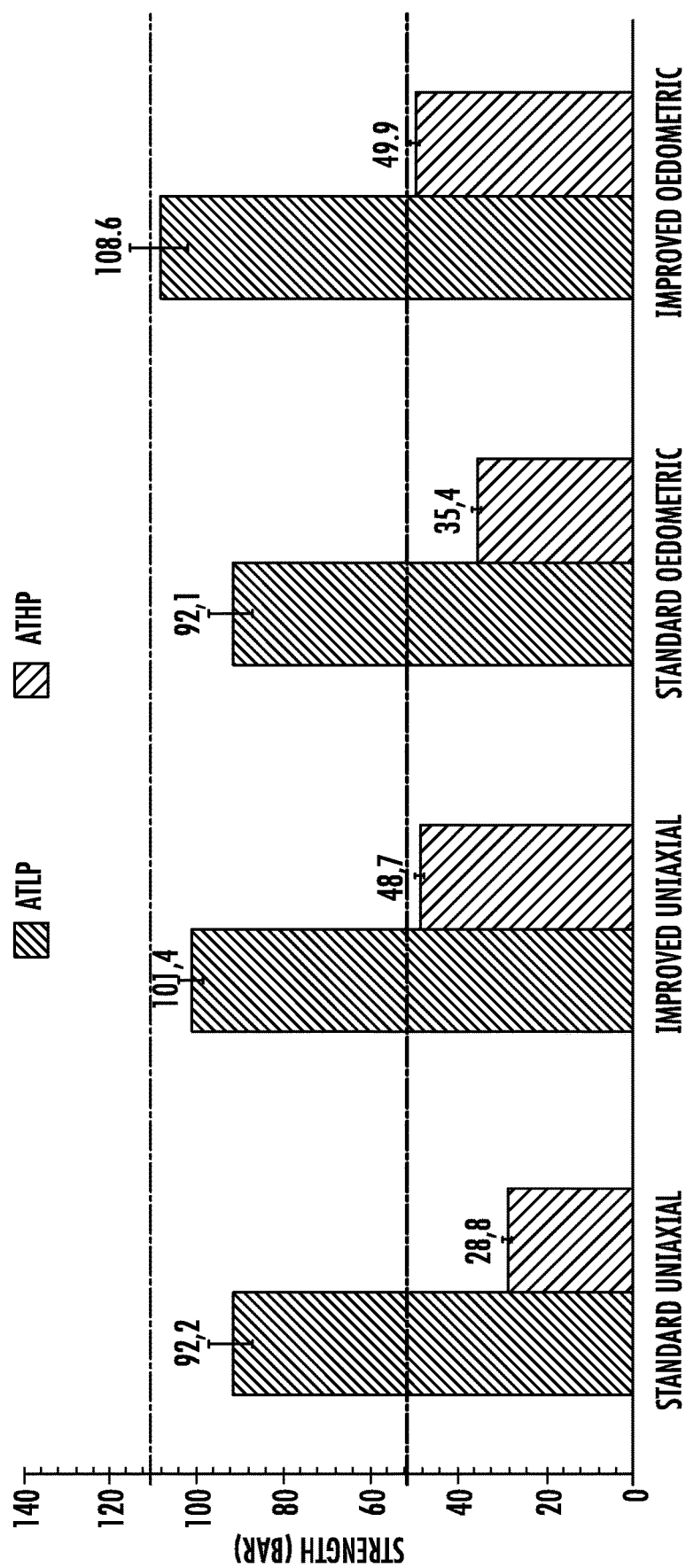

FIG. 13 presents graphical plot of data showing ATHP and ATLP uniaxial strength measurements approach the strength of the actual product under testing conditions according to these exemplary embodiments of the disclosure.

Figure 14A:
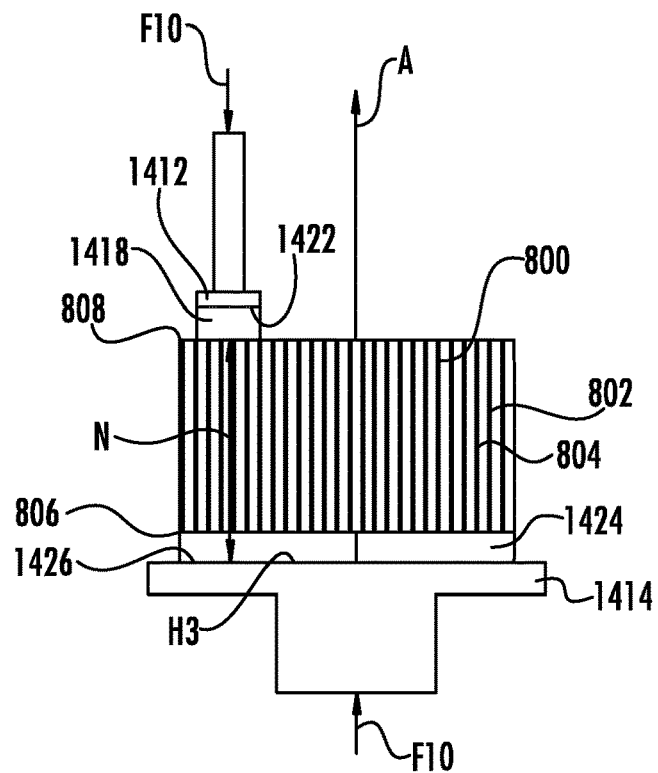
Figure 14B:
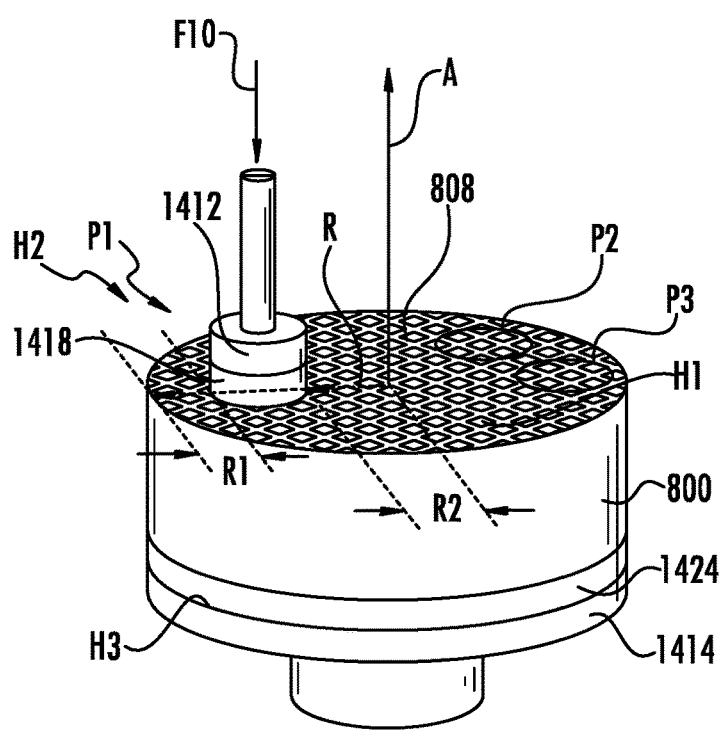

FIGS. 14A and 14B show mechanical apparatus set-up for compressive strength of a high porosity ceramic honeycomb body in an uniaxial A-axis test having an interlayer according to exemplary embodiments of the disclosure.

Figure 15A:
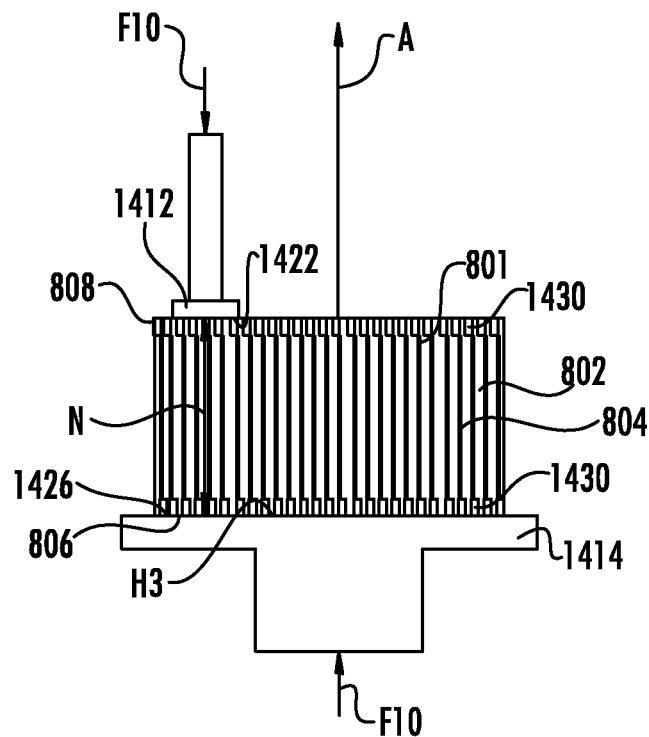
Figure 15B:
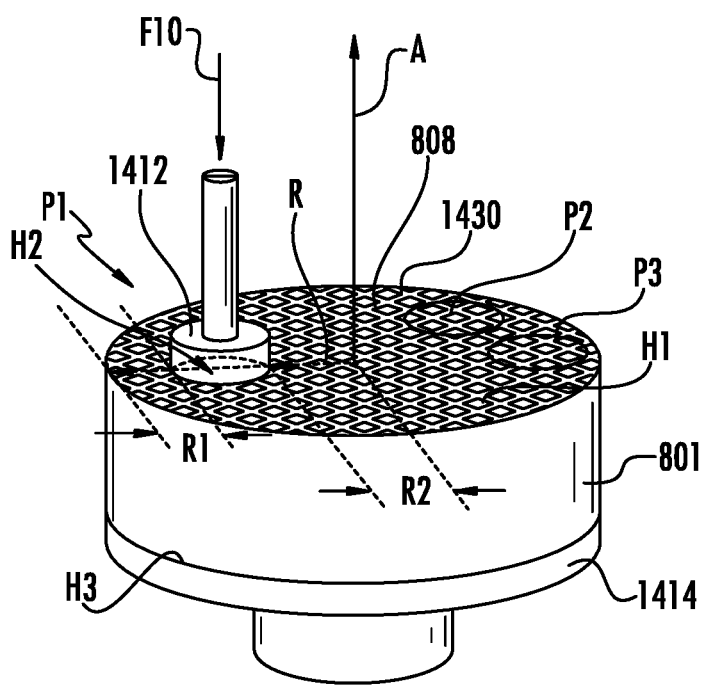

FIGS. 15A and 15B show mechanical apparatus set-up for compressive strength of a high porosity ceramic honeycomb body in an uniaxial A-axis test without an interlayer according to exemplary embodiments of the disclosure.

Figure 16A:
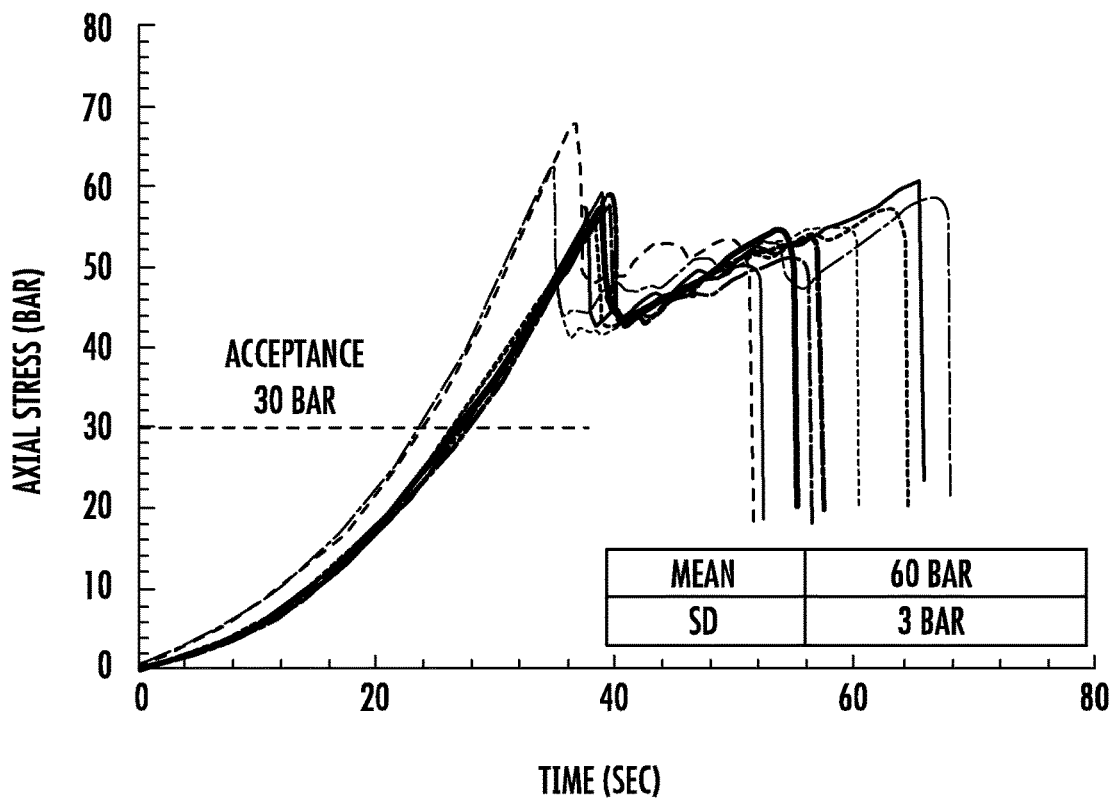
Figure 16B:
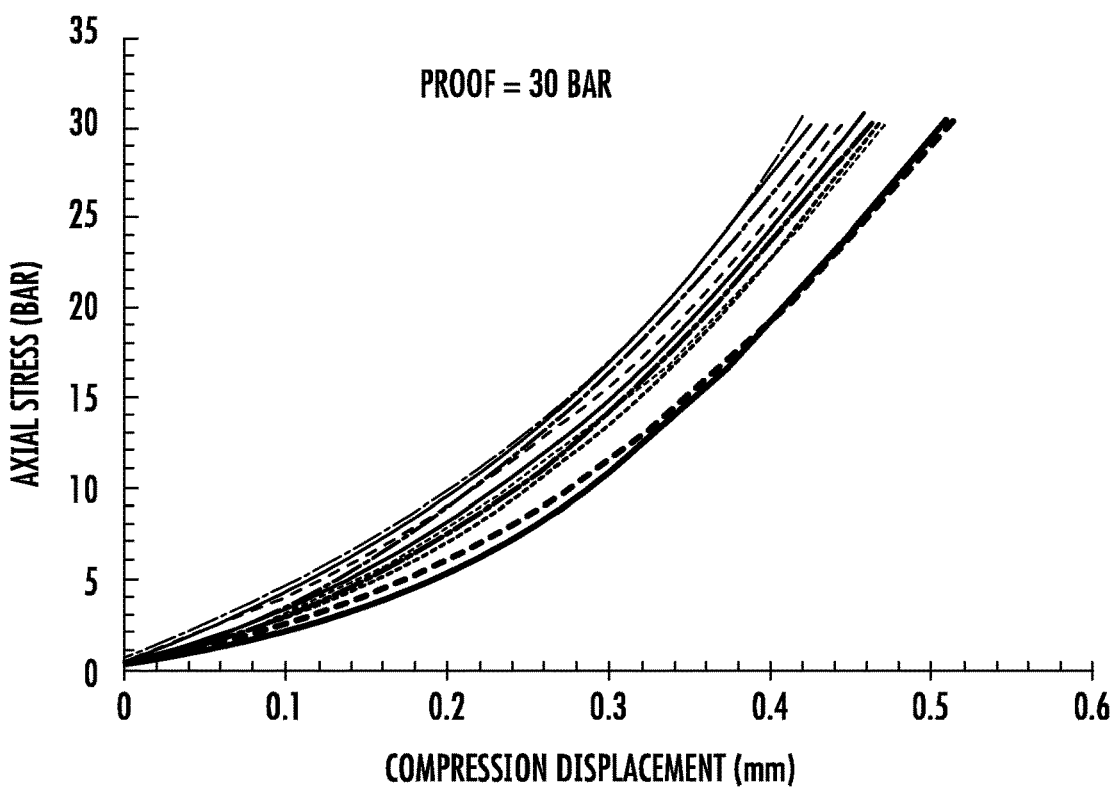
Figure 16C:
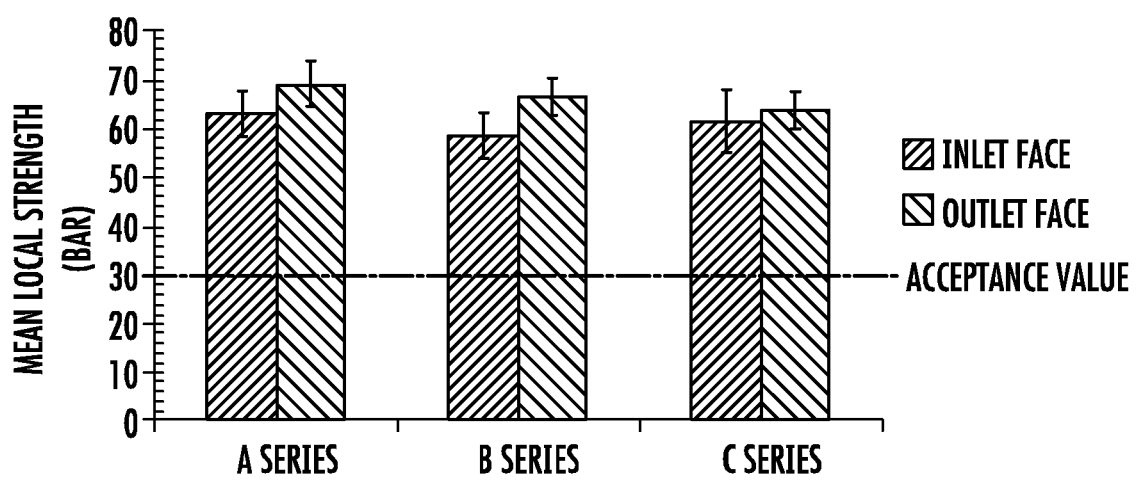

FIG. 16A presents a graphical plot of data showing mechanical strength of ATHP plugged honeycomb bodies tested in apparatus of FIGS. 15A and 15B. FIG. 16B presents a graphical plot of data showing proof testing results of ATHP plugged honeycomb bodies tested in apparatus of FIGS. 15A and 15B. FIG. 16C presents results for 90 local stamping tests on 18 different AT HP filters.

Figure 17A:
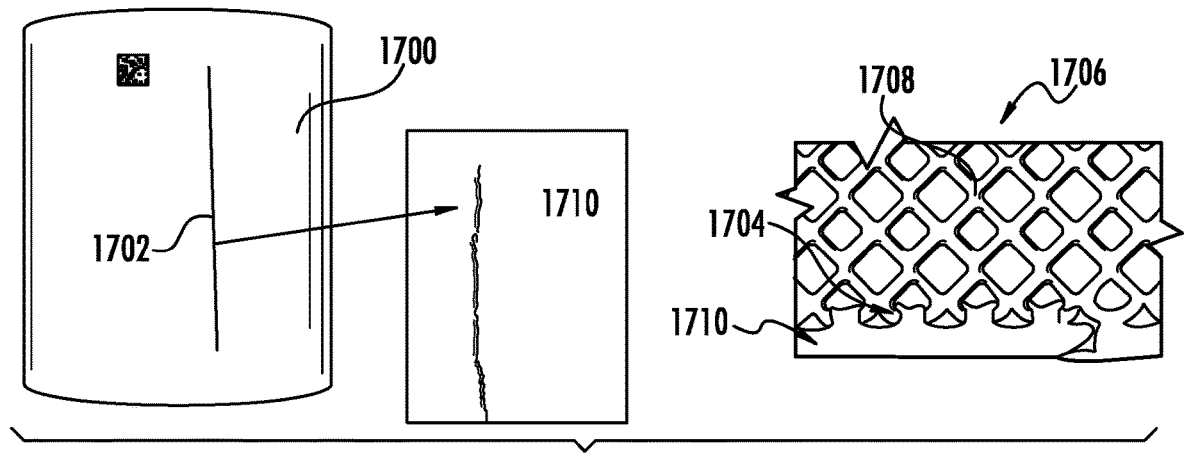
Figure 17B:
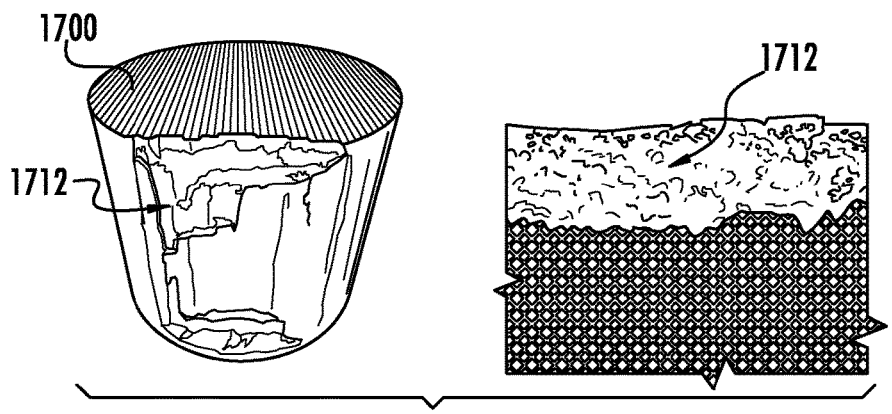
Figure 17C:
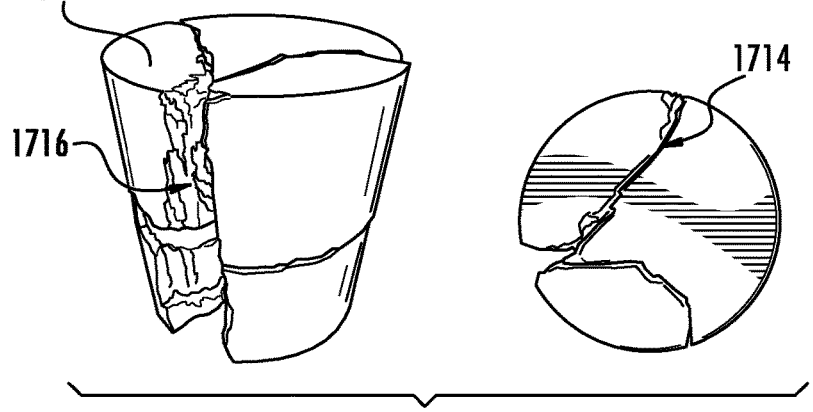

FIGS. 17A, 17B, and 17C illustrate failure modes 1, 2, and 3, respectively, for honeycomb bodies in three-dimensional (3D) isostatic strength tests.

Figure 18:
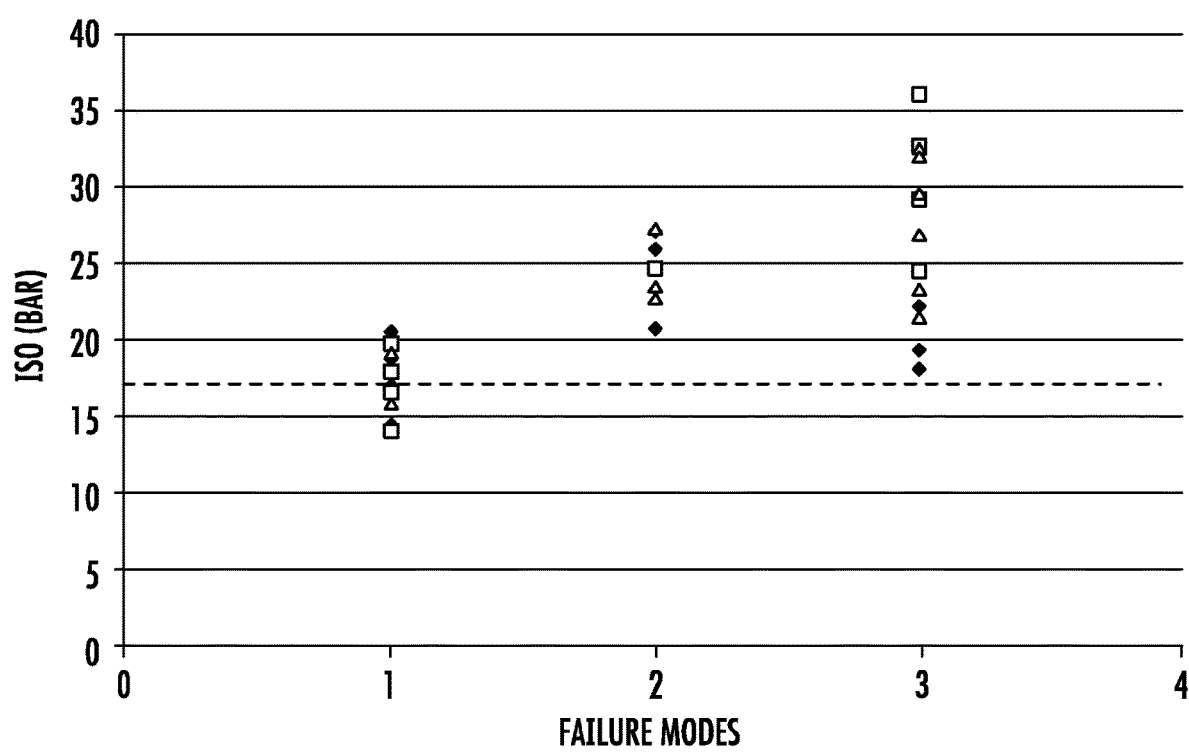

FIG. 18 is a graphical plot of data showing honeycomb body failure modes versus isostatic pressure indicating skin/web interface strength may drive isostatic strength.

Figure 19A:
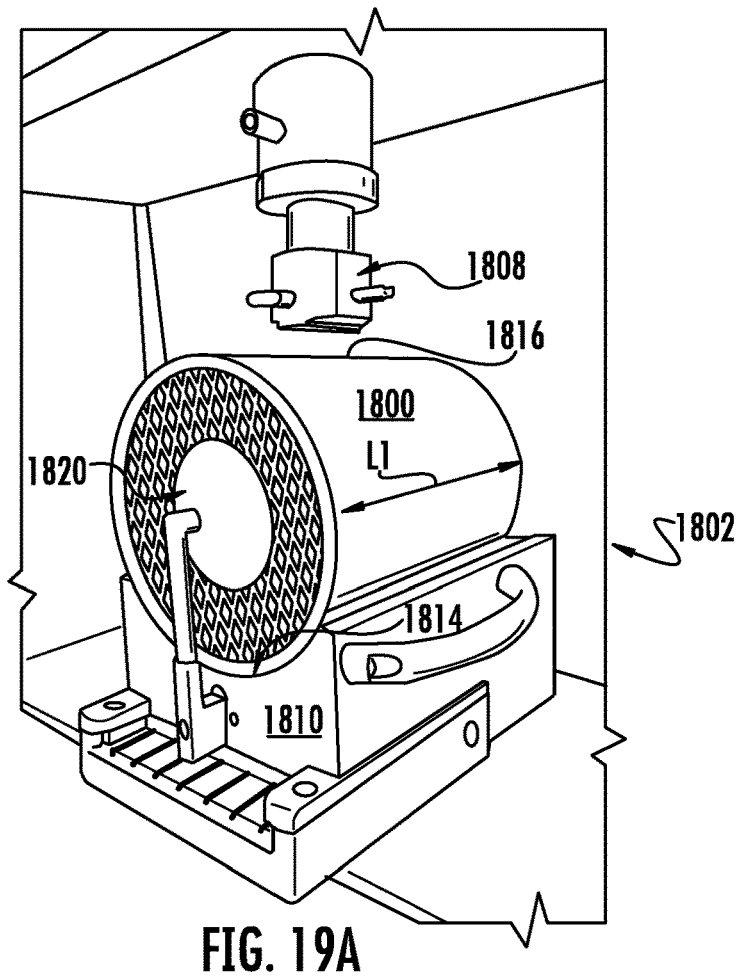
Figure 19B:
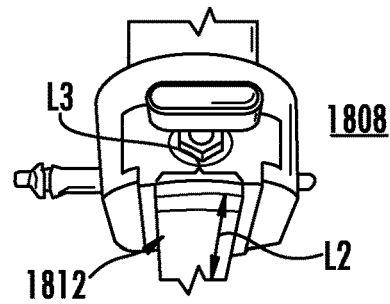
Figure 19C:
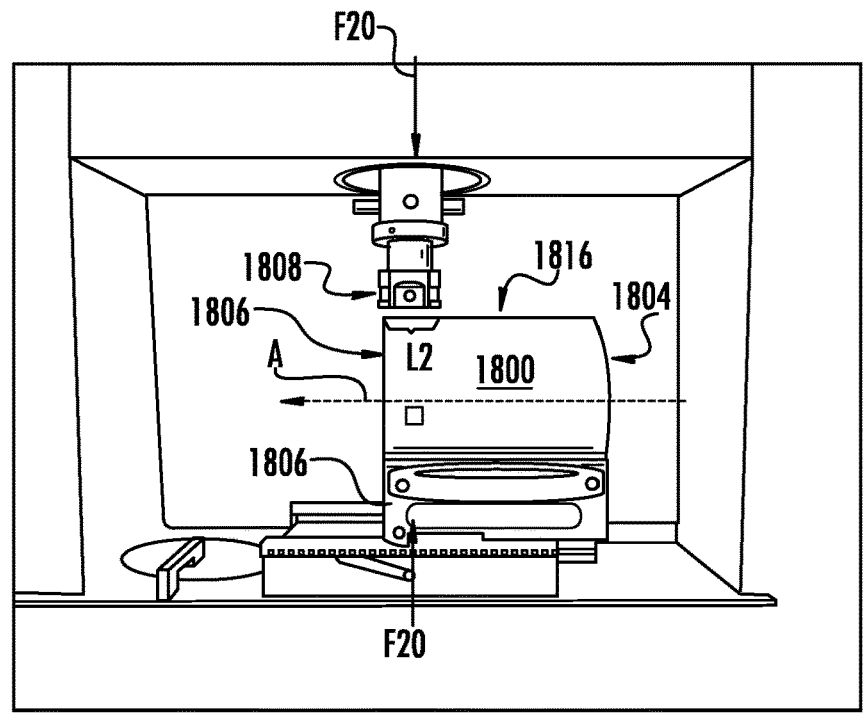

FIG. 19A is an isometric perspective view of a honeycomb filter in a horizontal stamping apparatus according to exemplary embodiments of the disclosure. FIG. 19B is a detail isometric perspective view of an upper platen in the horizontal stamping apparatus shown in FIG. 19A. FIG. 19C is a side view of the honeycomb filter in the horizontal stamping apparatus of FIG. 19A.

Figure 20A:
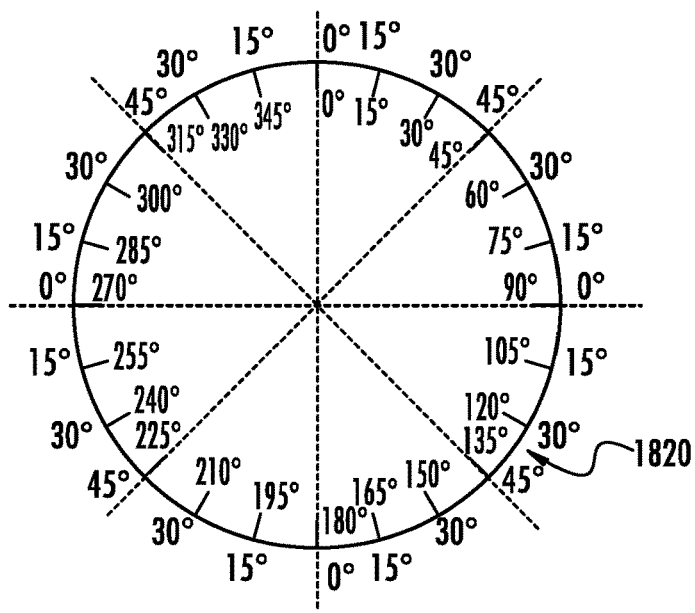
Figure 20B:
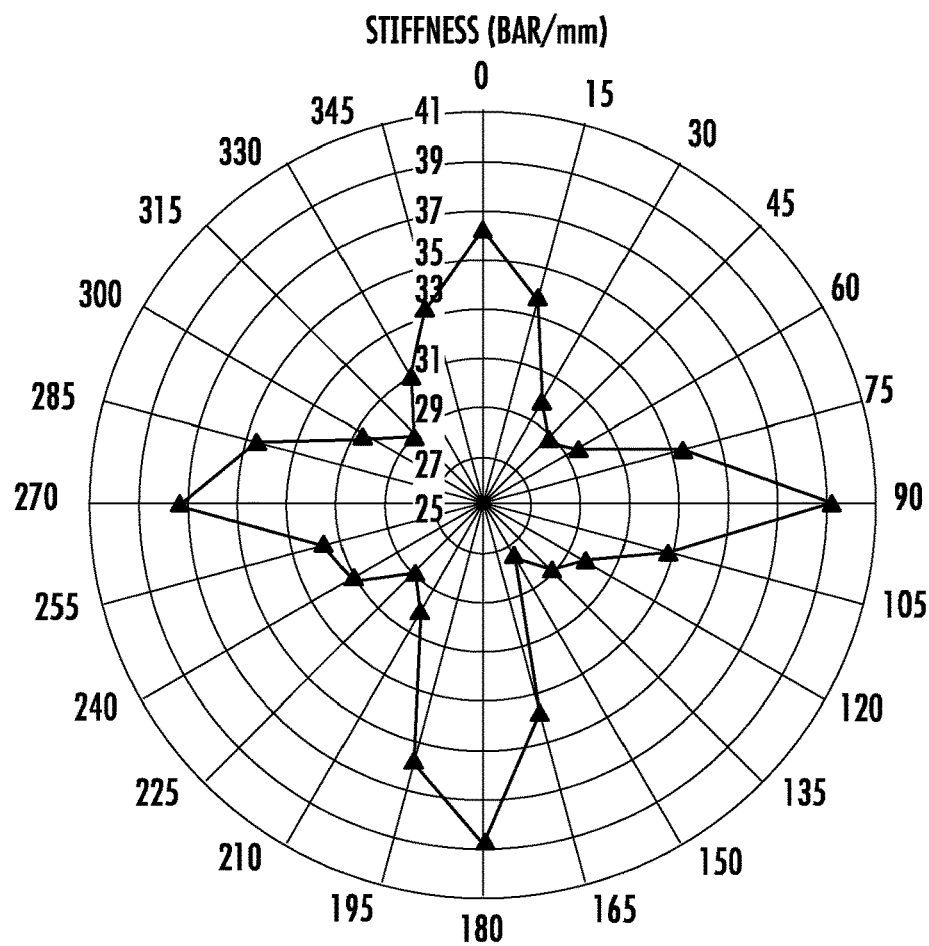

FIG. 20A illustrates an angular study to determine local stiffness by horizontal stamping according to exemplary embodiments of the disclosure. FIG. 20B presents a graphical plot of data showing local honeycomb body filter stiffness for a square cell geometry quantified by horizontal stamping according to exemplary embodiments of the disclosure.

Figure 21:
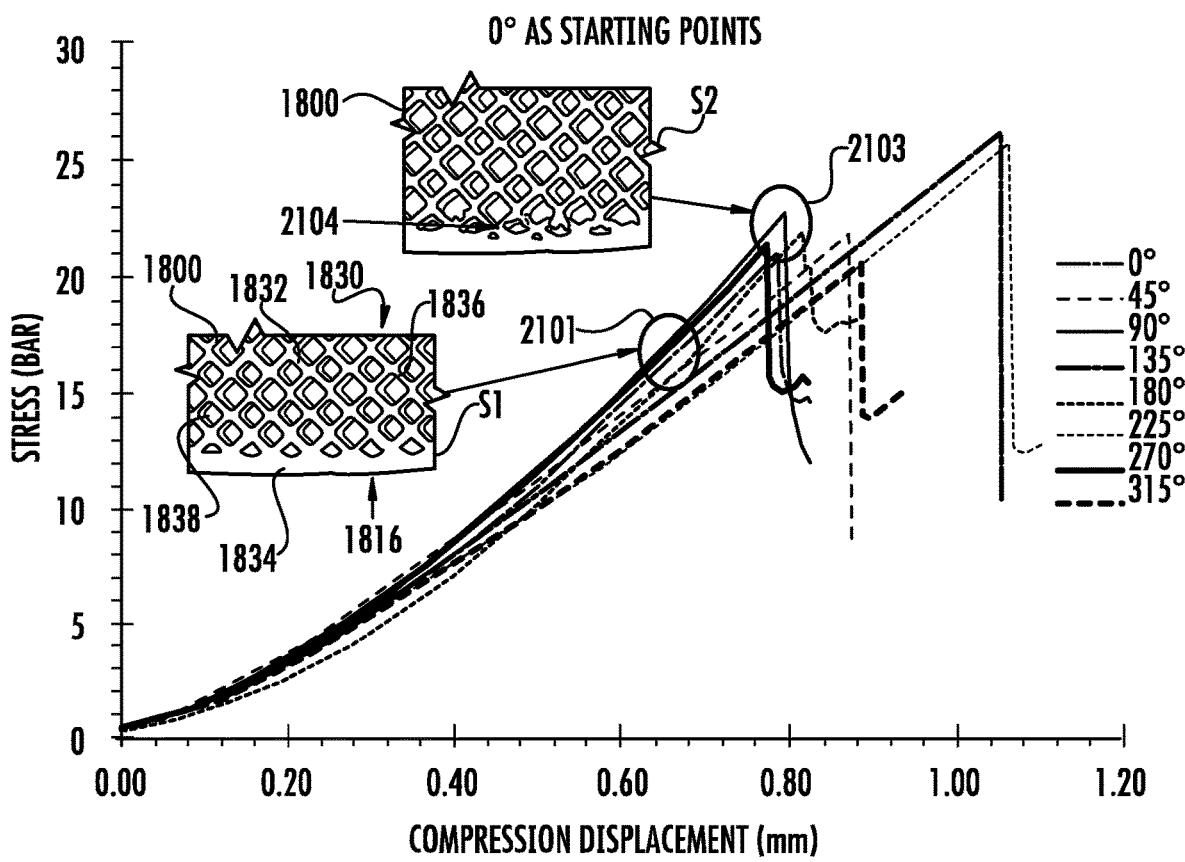

FIG. 21 is a graphical plot of data showing horizontal stamping strength of a porous ceramic honeycomb filter.

FIG. 22A illustrates mode 1 failure by isostatic strength testing of a porous ceramic honeycomb filter and FIG. 22B illustrates mode 1 failure produced by horizontal stamping according to exemplary embodiments of the disclosure indicative of the isostatic strength of the porous ceramic honeycomb filter.

Figure 23:
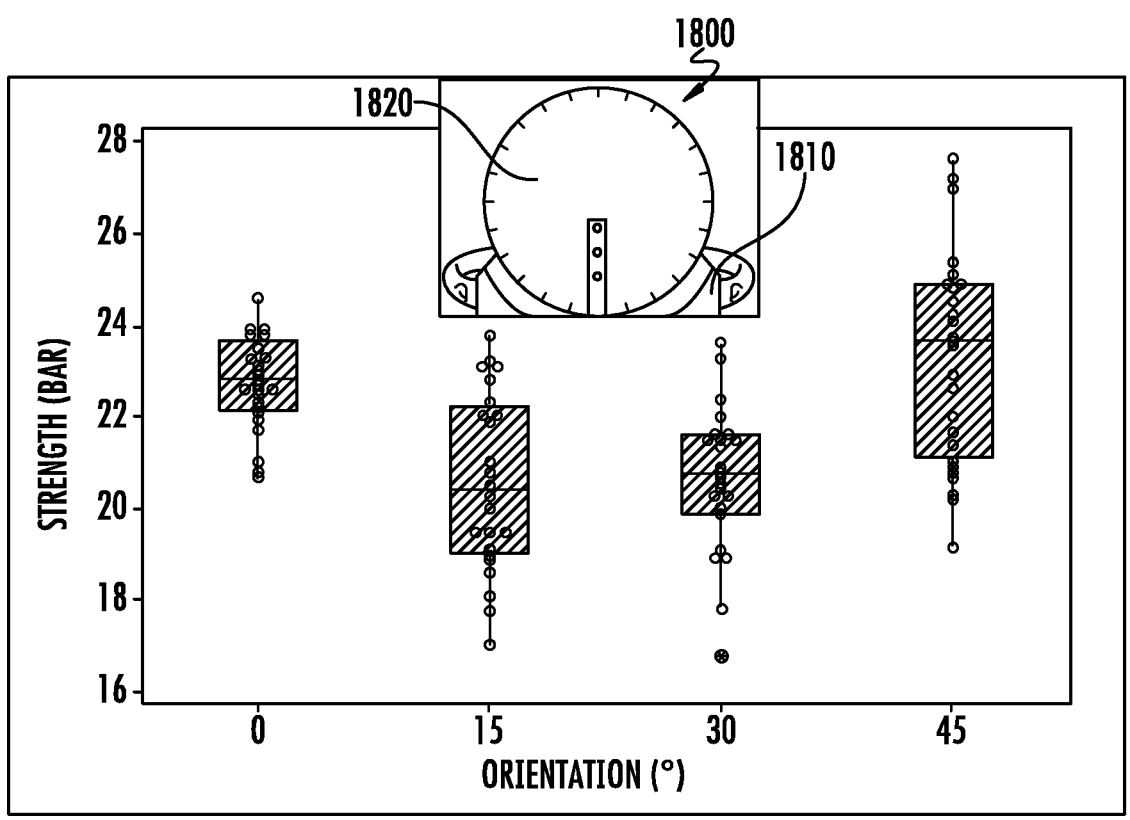

FIG. 23 is a graphical plot of data showing horizontal stamping strength variability from 0° to 45° for a square cell geometry of a porous ceramic honeycomb filter.

Figure 24A:
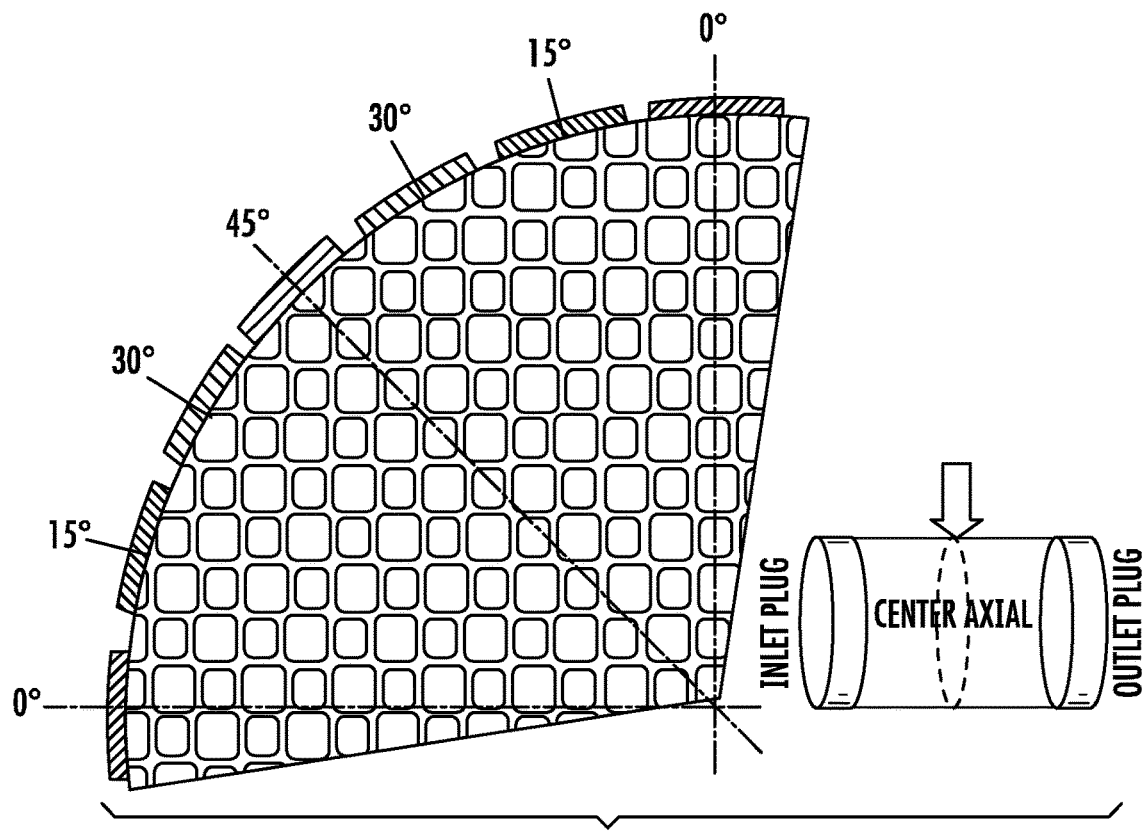
Figure 24B:
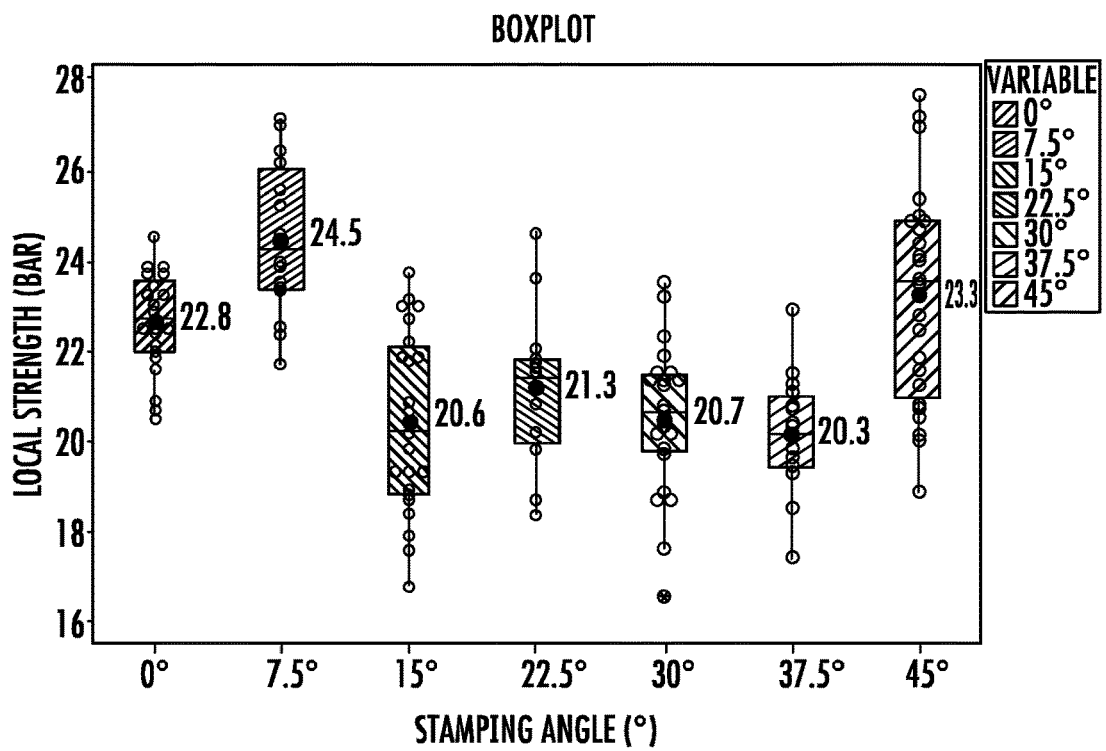

FIGS. 24A and 24B show that close to center, between end faces axially, local strength varies with stamping angle. The weakest zone was detected between 15° and 37.5°.

Figure 25:
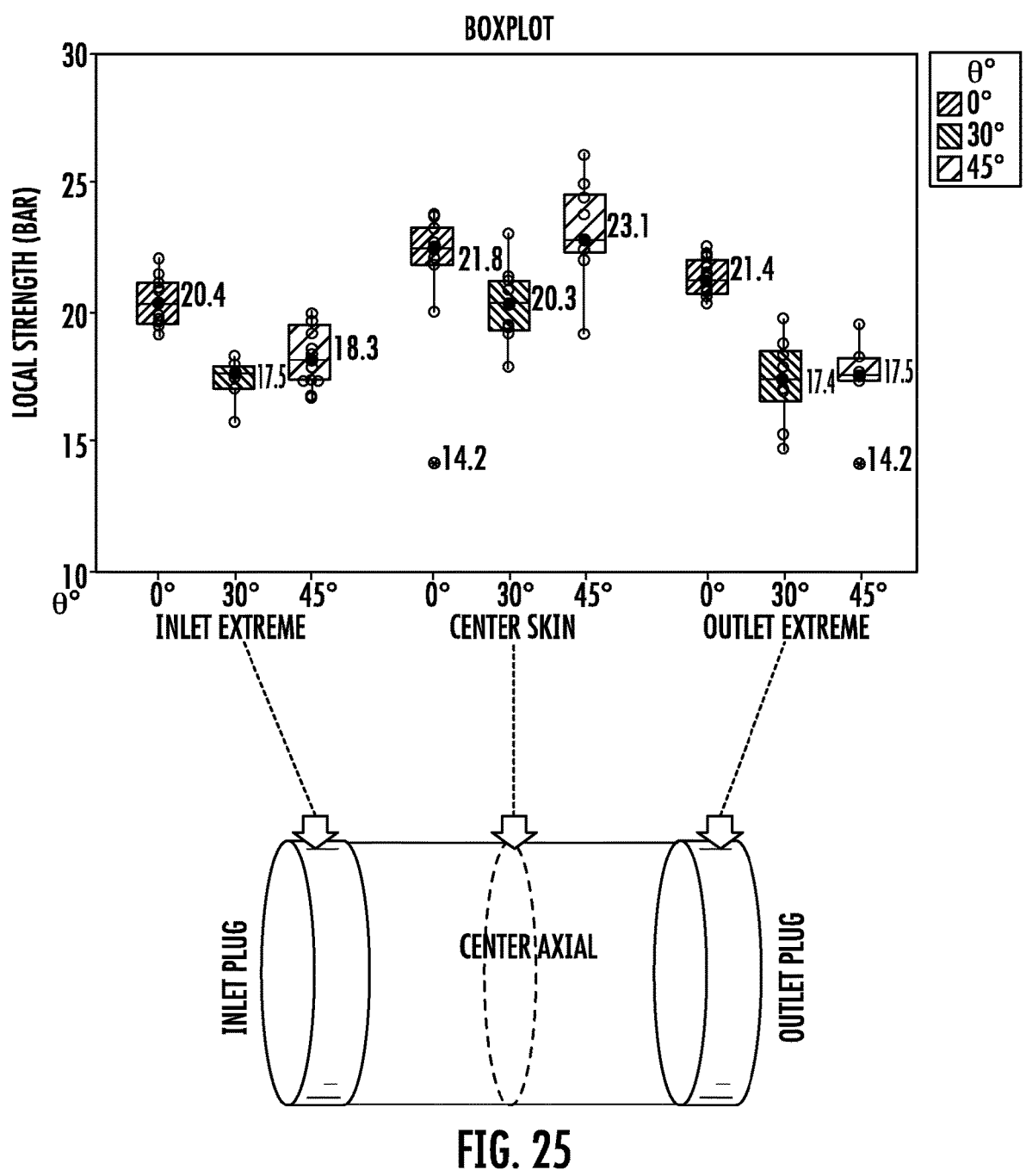

FIG. 25 is a graphical plot of data showing horizontal stamping strength variability along the axial length for a square cell geometry of a porous ceramic honeycomb filter.

DETAILED DESCRIPTION

The manufacture of porous ceramic honeycomb bodies may be accomplished by the process of plasticizing ceramic powder batch mixtures, extruding the mixtures through honeycomb extrusion dies to form honeycomb extrudate, and cutting, drying, and firing the extrudate to produce ceramic honeycomb bodies of high strength and thermal durability having channels extending axially from a first end face to a second end face. As used herein a ceramic honeycomb body includes ceramic honeycomb monoliths and ceramic segmented honeycomb bodies.

A co-extruded or an after-applied exterior skin may form an outer axial peripheral surface of the ceramic honeycomb bodies. Each channel of the honeycomb bodies defined by intersecting walls (webs), whether monolithic or segmented, can be plugged at an inlet face or an outlet face to produce a filter. When some channels are left unplugged a partial filter can be produced. The honeycomb body, whether monolithic or segmented, can be catalyzed to produce a substrate. Further, filters and partial filters can be catalyzed to provide multi-functionality. The ceramic honeycomb bodies thus produced are widely used as catalyst supports, membrane supports, as wall-flow filters, as partial filters, and as combinations thereof for cleaning fluids such as engine exhausts.

Among the commercially successful processes for ceramic honeycomb body manufacture are those that utilize large co-rotating twin screw extruders for the mixing and extruding of ceramic honeycomb extrudate. Ram extrusion, pressing, casting, spraying and 3-dimensional printing are other processes for ceramic honeycomb body manufacture. Ceramic honeycomb body compositions are not particularly limited and can comprise major and minor amounts of cordierite, aluminum-titanate, mullite, β-spodumene, silicon carbide, zeolite and the like, and combinations thereof.

Ceramic honeycomb bodies may be disposed in a metal vessel in an exhaust system. The vessel may be referred to as a can and the process of disposing the ceramic honeycomb body in the can may be referred to as canning.

Exemplary embodiments of the disclosure provide an apparatus to mechanically test ceramic honeycomb bodies. Typical cell wall thicknesses can range from about 0.025 mm to about 1.5 mm. As used herein, the term "honeycomb" is intended to include a generally honeycomb structure but is not strictly limited to a square structure. For example, hexagonal, octagonal, triangular, rectangular or any other suitable shape may be used. Typical pore sizes contained within the porous walls can be from 0.1 μm to about 100 μm, with cell wall porosity between about 15% and 75%, for example, between about 25% and 60%. To increase catalyst quantity and minimize pressure drop, high porosity filters, for example, porosities of about 45% and above, for example, porosities of about 50% to about 70%, are being developed.

Since mechanical performance, for example, compressive strength or shear strength, can be a function of porosity, it is important to assess the mechanical performance of the high porosity products. Several tests may be performed to assess mechanical performance, for example, flexure testing, isostatic testing, tensile testing, compression testing, and the like. In particular, compression testing is of interest since it assesses the materials behavior during assembly processes, for example, canning, and during use, for example, axial stress due to vibration or thermal expansion.

Figure 1:
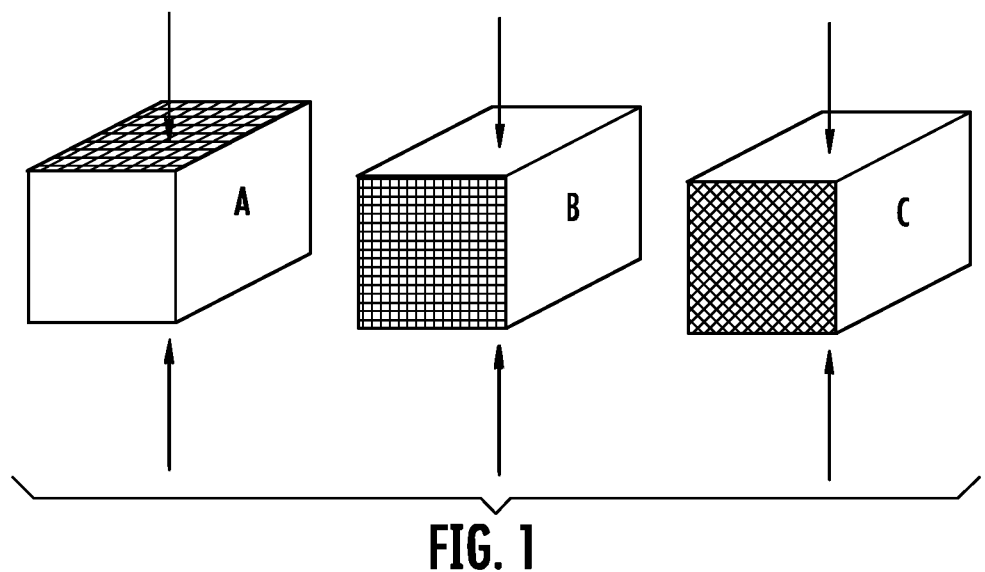
FIG. 1 presents a schematic view of A-axis, B-axis, and C-axis types of compressive tests on ceramic honeycomb bodies.

To assess compressive strength, either multi-axial loading, such as two-dimensional (2D) or three-dimension (3D) isostatic strength, or uniaxial loading, such as A-axis, B-axis, or C-axis as shown in FIG. 1, can be applied on a regular basis such as for product development and/or quality control.

Figure 2A:
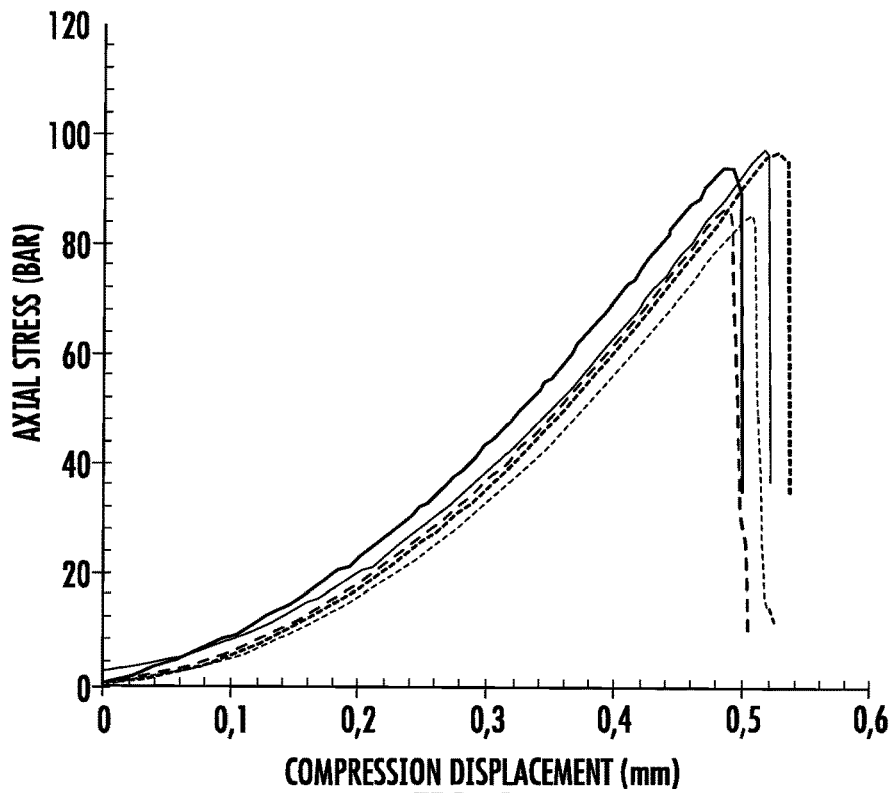
FIG. 2A is a graphical plot of data showing uniaxial compressive loading using core-drilled samples of ATLP (Low Porosity Aluminum Titanate) and FIG. 2B is a graphical plot of data showing uniaxial compressive loading using core-drilled samples of ATHP (High Porosity Aluminum Titanate).
Figure 2B:
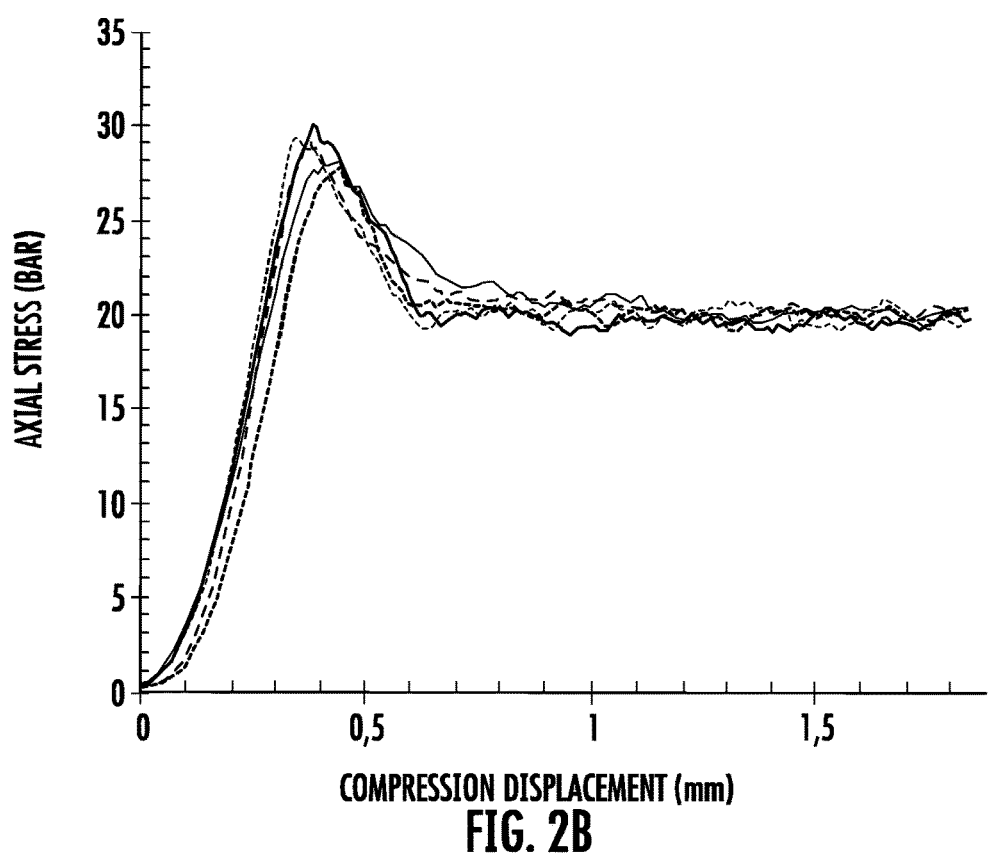

A-axis testing is typically used as a quality control test in order to assess the strength and provide any change validation. Changes may include process changes such as firing cycle timing, kiln loading densities, and the like, or design changes such as cell size, web thickness, and the like. As shown in FIG. 2A, for 1 inch (2.54 cm) diameter by 1 inch (2.54 cm) height specimens the A-axis test is accurate for low porosity materials since it shows a standard brittle material stress-strain curve. However, as presented in FIG. 2B, for the same size specimens, when high porosity material is considered, the inventors found that the curve shape was unusual. The inventors identified the question of the accuracy of the A-axis test for assessing the compressive strength of high porosity ceramic honeycomb bodies.

Figure 3:
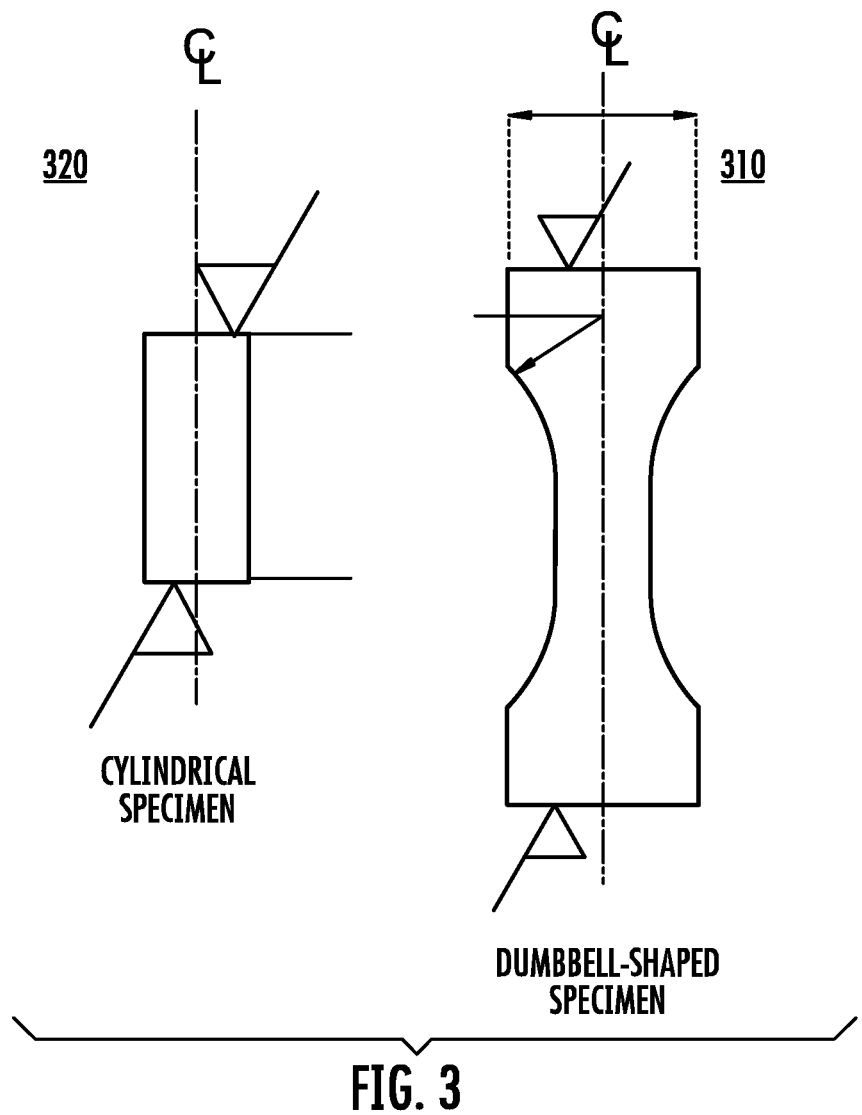
FIG. 3 presents a schematic view of two kinds of specimen geometries proposed by the ASTM C1424 for compressive strength of advanced ceramics.

Two standardized (ASTM C1424) compression testing samples are shown in FIG. 3. The dumbbell-shaped specimen 310 avoids inducing stress singularity. However, it requires a relatively complex preparation. The cylindrical specimen 320 has the advantage of a relatively easier preparation, for example, by core-drilling. However, the cylindrical specimen 320 can induce edge effects. For the cylindrical specimen 320, the edge effects can be due to several aspects. For example, stress concentration caused by sectional change from loading platens (loading platters) to specimen. Also, deficient surface quality of the cylindrical specimen, for example, uneven face surface, can induce stress concentration. Disparities of mechanical properties, for example, Young's modulus, Poisson's ratio, between loading platens and the specimen can also induce stress concentration. The cylindrical specimen testing also enables lateral displacement that is dependent on Poisson's ratio and the amount of friction between the platens and the sample. A theoretically perfect uniaxial compressive testing does not allow any friction between the platens and the sample faces.

Figure 4A:
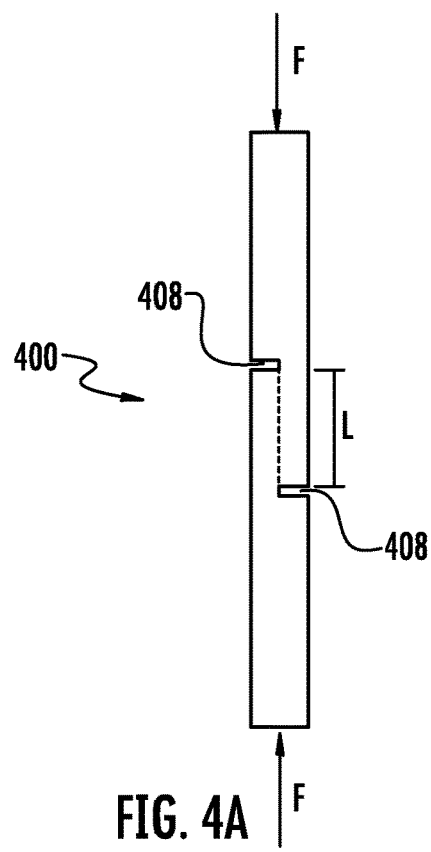
FIG. 4A presents a schematic of a double-notched specimen used for shear strength assessment and FIG. 4B presents a sample after shear testing.
Figure 4B:
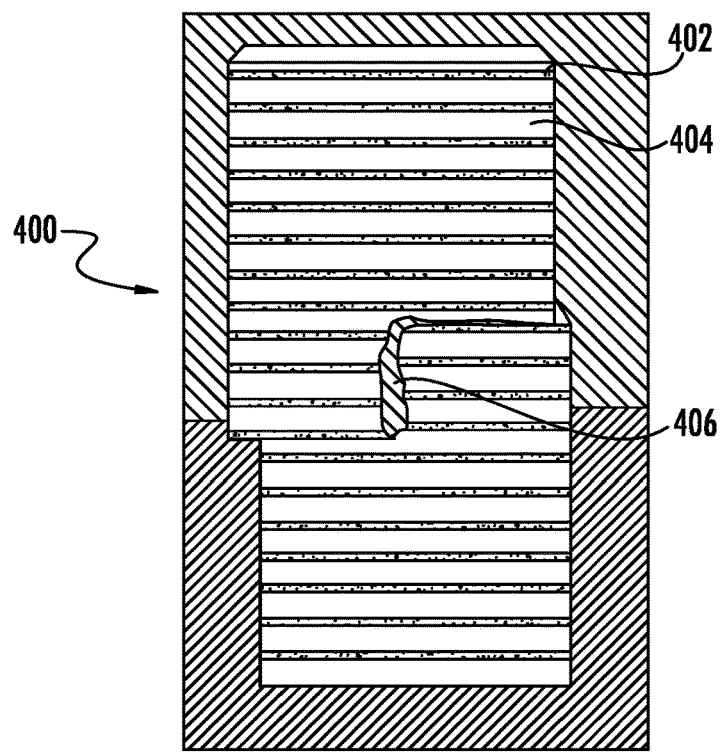

Other sectional geometries can be used for assessing the compressive (or other mechanical loading) properties. For example, the geometries can be rectangular or square cross sections. The test specimens can be notched or un-notched. FIG. 4A shows a rectangular specimen 400 that is double-notched. The macroscopic loading of such a specimen consists in applying compressive forces "F" on both faces. These loads are transformed to shear loading by means of sample geometry. FIG. 4B shows the double-notched specimen 400 used for shear strength assessment after shear testing. Intersecting porous ceramic walls 402 that define channels 404 therebetween are traversed by fracture surface 406 between notches 408. The discovery disclosed in exemplary embodiments herein as described in further detail below can be applied to loading that is transmitted by means of platens, loading that involves rigid-to-rigid contact between loading device and the specimen, and the like.

Figure 5:
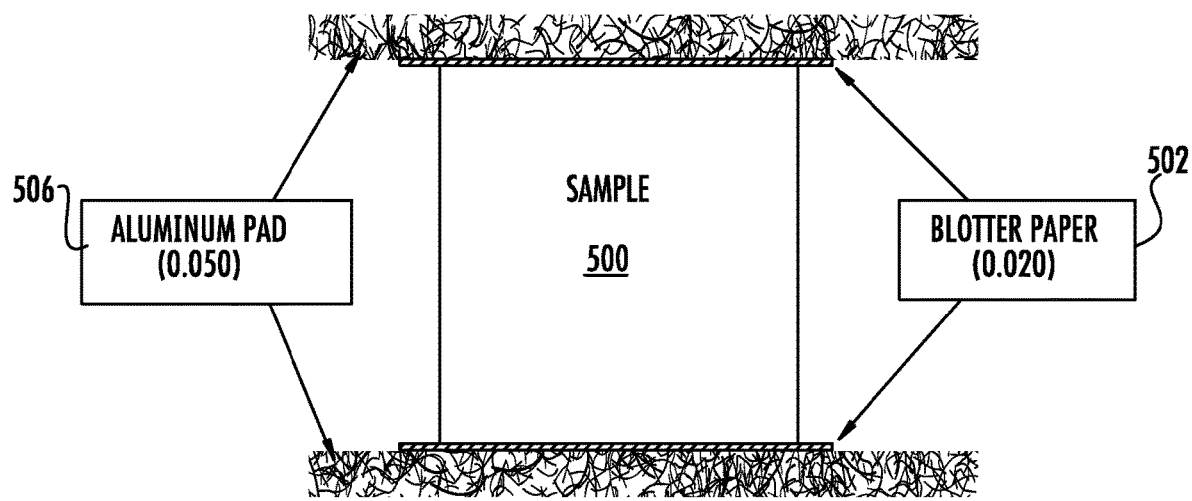
FIG. 5 shows a schematic of an architecture used for axial compressive testing.

To overcome issues related to compression testing using non dumbbell specimen, for example cylindrical or rectangular specimen, a compliant layer can be used. The compliant layer can be paper, metallic thin foil, a polytetrafluoroethylene (PTFE) (Teflon®)) layer, or a combination thereof, such as paper and metallic thin foil as shown in FIG. 5, or a combination of these and a Teflon® layer. FIG. 5 shows a schematic of an architecture used for axial compressive testing of a specimen 500 having 0.02 inch (0.51 mm) thick blotter paper 502 and 0.05 inch (1.3 mm) thick aluminum pad 506 disposed between the specimen 500 and loading platens (not shown). These layers work adequately for low porosity material specimens. However, they are insufficient for high porosity material specimens where the individual webs are not strong enough to correctly transmit the loads from loading platen/specimen interface along the specimen webs.

A sufficient compression test using non-dumbbell samples can, amongst other aspects, reduce edge effect, allow lateral displacement, and compensate for potential uneven specimen load surfaces. According to exemplary embodiments of the disclosure, an improved layer (interlayer) comprised of Teflon®/mat/Teflon® provides reduced edge effect, lateral displacement, and compensates for potential uneven specimen load surfaces.

Exemplary embodiments disclose an interlayer, including a layer or an assembly of layers, allowing accurate measurement of the compressive mechanical properties of high porosity materials. The disclosed interlayer also allows measurement of lower porosity materials, for example, porosities of about 45% and below. Accordingly, the disclosed interlayer eliminates or reduces local singularities and overcomes the intrinsic porous web weakness and the web's non-ability to sufficiently transmit loads during testing. Exemplary embodiments of the disclosure are not limited to the specific layers mentioned herein, but also include other soft internal materials, such as foams, other types of ceramic or polymer fibers or fabrics, and the like. Exemplary embodiments also provide for other sample orientations than A-axis, for example, B-axis, C-axis, etc.

Exemplary embodiments provide a mechanical testing apparatus to test the mechanical strength of a specimen of material. The apparatus includes a first platen and a second platen comprising facing surfaces configured to apply a force to the specimen of material when disposed between the facing surfaces of the first platen and the second platen. The apparatus includes at least one intermediate platen configured to be disposed between at least one of the facing surface of the first platen and the specimen of material, and the facing surface of the second platen and the specimen of material, wherein the first platen and the second platen have a hardness greater than the at least one intermediate platen. The apparatus includes a controller configured to monitor a result when force is applied to the specimen disposed between the first platen and the second platen. The at least one intermediate platen comprises a surface weight of about 350 g/m$^2$ and a thickness in a direction N between the facing surfaces of the first platen and the second platen of at least about 20 mm.

The intermediate platen allows accurately measuring the compressive mechanical properties of high porosity materials. Exemplary embodiments also disclose using the intermediate platen for accurately measuring the compressive strength of high porosity materials. As used herein, the intermediate platen refers to interchangeably, an interlayer, an intermediate layer, a layer, and/or a combination of layers configured to be disposed between a platen and the test specimen. The intermediate layer can be a layer or a combination of layers and can be used for different sample geometries, for example, dumbbell, cylindrical, rectangular, notched, etc. The intermediate layer provides an improvement in strength test results when there is a significant difference of physical properties (e.g., stiffness, Young's modulus, hardness, etc.) between loading devices (platens) and the tested material specimen. For example, the loading devices can have a Rockwell hardness of 981 to 1471 HRC. In particular, the intermediate layer is convenient for high porosity materials. The intermediate layer reduces the edge effects and the stress concentration effects. The intermediate layer provides a good transmission of efforts from the loading devices to the test specimen.

The intermediate layer includes at least one highly soft layer. Highly soft as used herein refers to low unconstrained compressive modulus (<50 MPa) and high enough failure deformation (>10%). A preferred material has a compressive modulus at origin equal to 0.07 MPa and a tangent modulus (between 55% and 65%) equal to 4 MPa. The intermediate layer may have at least one highly soft layer and additional layers and the highly soft layer can be comprised of several layers that result in a highly soft layer when combined. The highly soft layer can be used for mechanical strength testing, for example, compression or shear using double notched specimen as described above with reference to FIGS. 4A and 4B. In general, exemplary embodiments of the intermediate layer provide an improvement to test results where loading is transmitted by platens and/or by rigid to rigid contact between loading device and the material specimen sample.

The intermediate layer comprises a surface weight of about 350 g/m$^2$ and a thickness in a direction N between the facing surfaces of the first platen and the second platen of at least about 20 mm. For example, the intermediate layer comprises a surface weight of about 150, 250, 350, 450, or 550 g/m$^2$. For example, the intermediate layer comprises a thickness of about 10, 15, 20, 25, 30 mm.

Figure 6A:
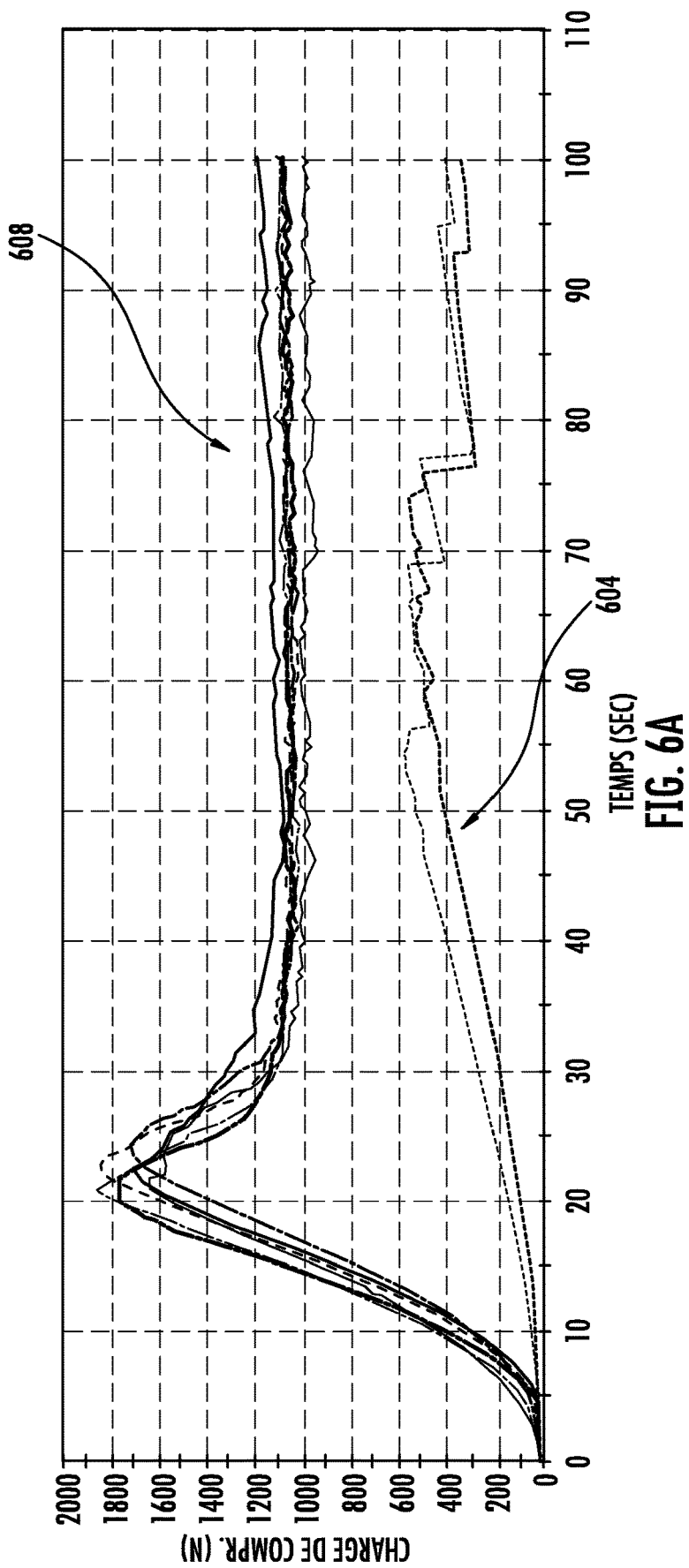
FIG. 6A is a graphical plot of data showing uniaxial compressive loading using core-drilled samples of ATHP and non-soft interlayers.
Figure 6B:
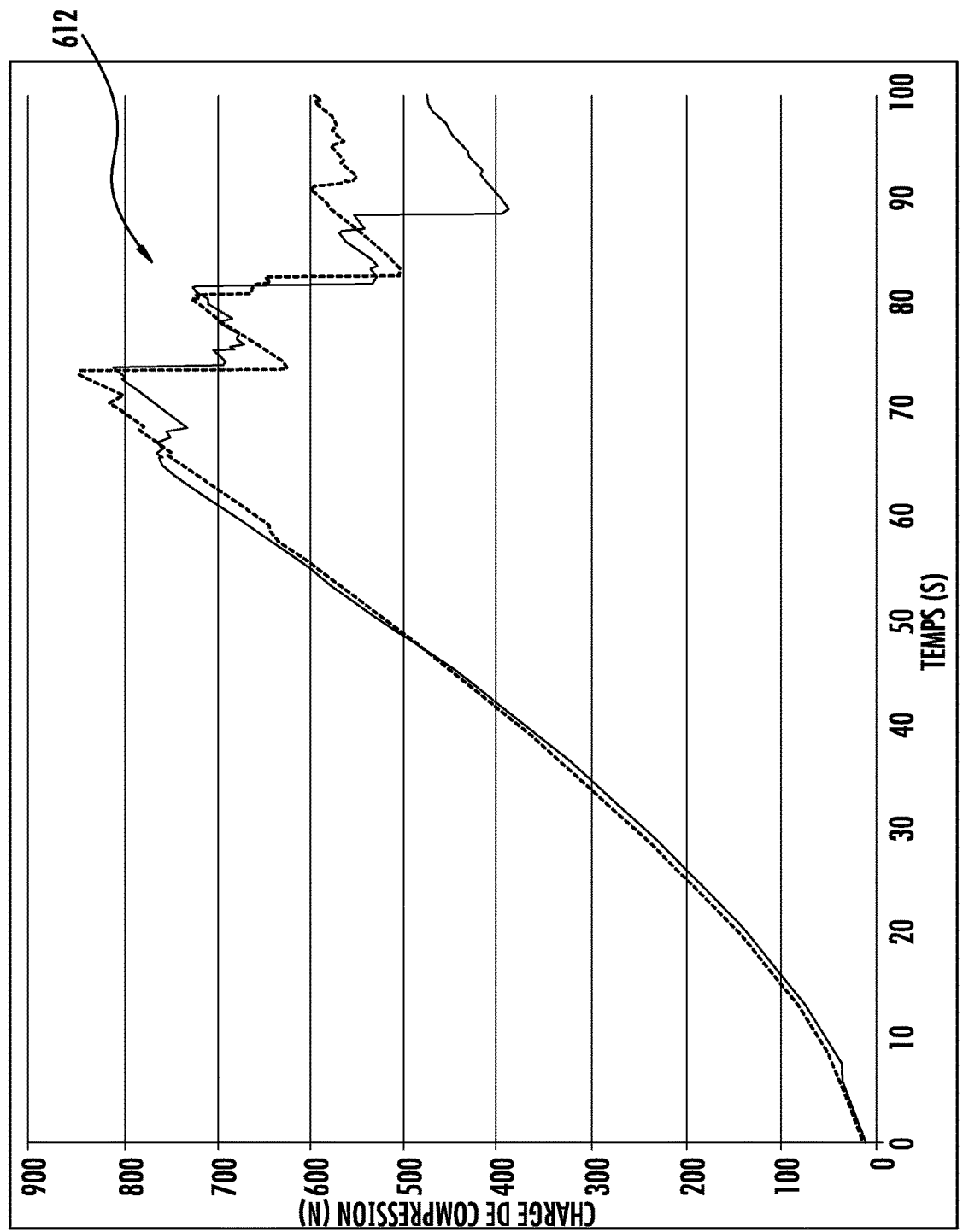
FIG. 6B is a graphical plot of data showing uniaxial compressive loading using core-drilled samples of ATHP and silicone rubber interlayers.

FIG. 6A is a graphical plot of data showing uniaxial compressive loading using core-drilled samples of ATHP and non-soft interlayers. FIG. 6B is a graphical plot of data showing uniaxial compressive loading using core-drilled samples of ATHP and silicone rubber interlayers. FIGS. 6A and 6B show how ATHP axial compressive strength remains low (average<3.5 MPa) when using non-soft interlayers such as aluminum, blotter paper, Teflon®, and the like. Aluminum, blotter paper, and Teflon®, (alumininum/blotter paper/Teflon®) was used in the tests resulting in the upper curves in FIG. 6A and silicone with Teflon® (silicone/Teflon®) was used in the lower curves. FIGS. 6A and 6B also show that when using non adequate soft layer such as a rubber-like material, stick-slip effects occur evidenced by the accidental curve shape. While not wishing to be bound by theory, this is believed to be due to the fact that rubber material is incompressible. So when applying the axial load, the rubber material tends to move laterally. But due to the high friction on one side, and ceramic sample lower displacement on the other side, a displacement mismatch is created between ceramic and rubber. This mismatch induces high stick-slip and frictional stresses. The result is a low strength value and inaccurate stress-strain curve as shown in FIG. 6B.

Figure 7A:
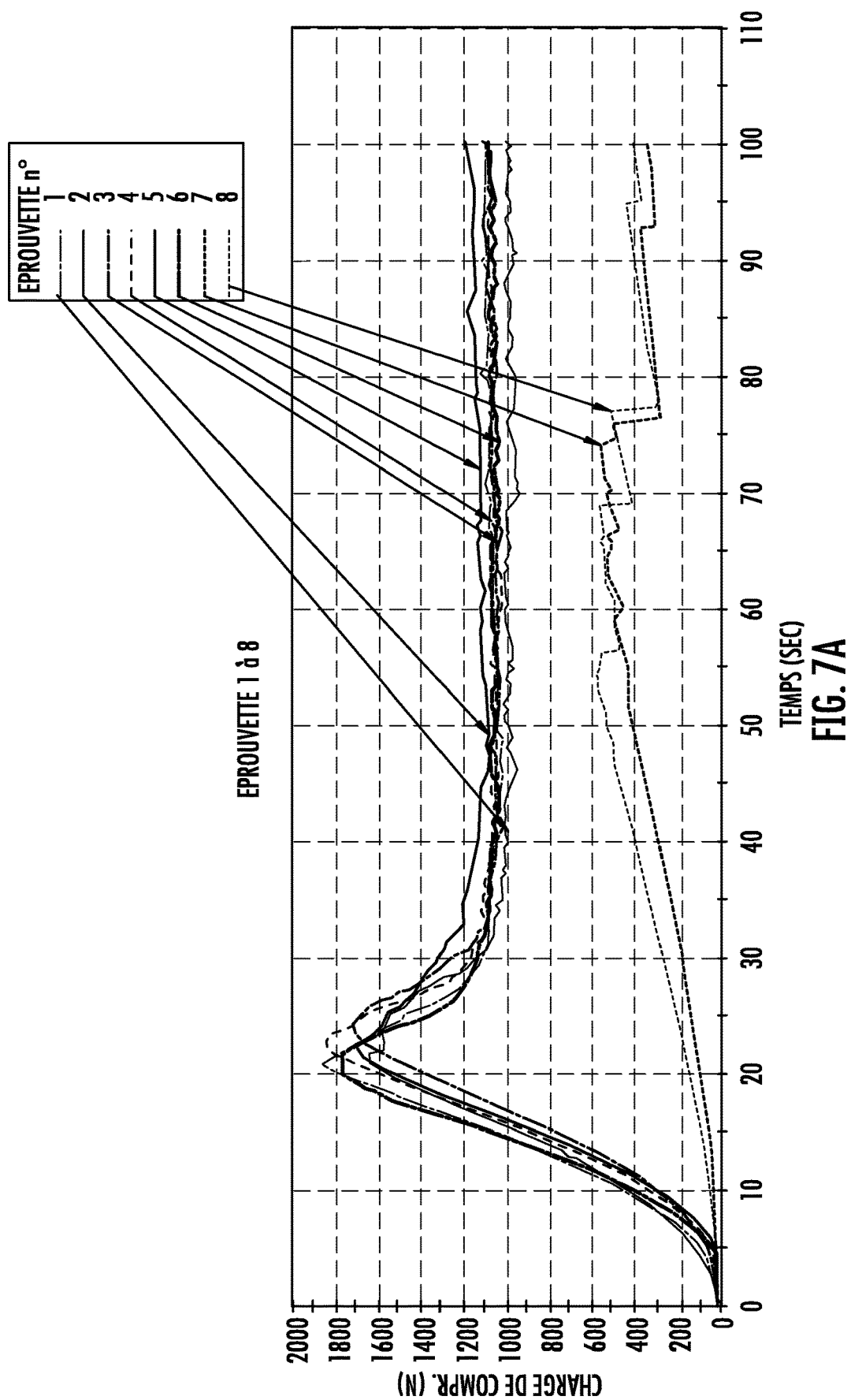
FIG. 7A shows a graphical plot of data showing uniaxial compressive loading using core-drilled samples of ATHP and various combinations of interlayer.
Figure 7B:
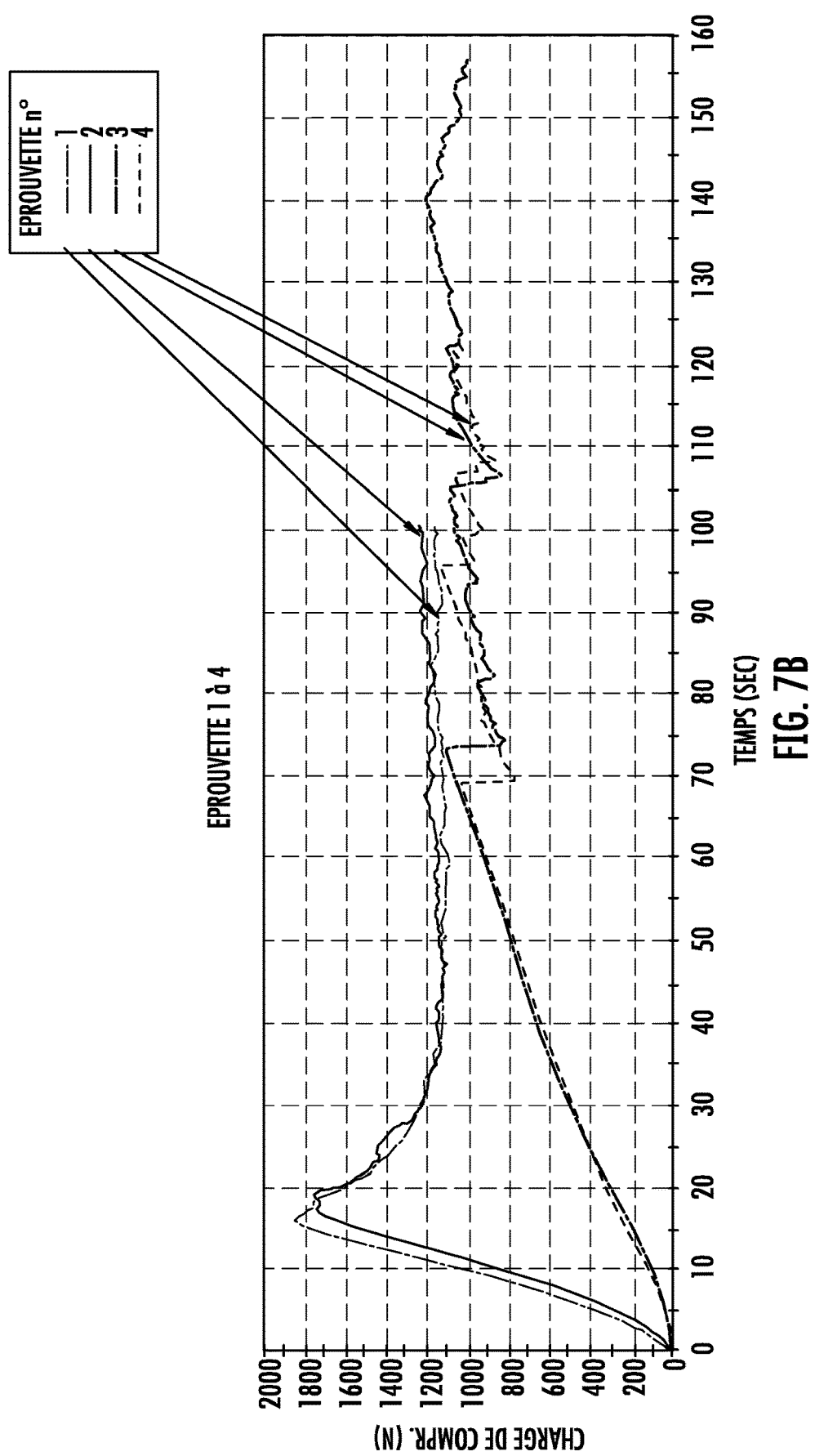
FIG. 7B shows a graphical plot of data showing uniaxial compressive loading using core-drilled samples of ATHP and non-soft interlayers and various combinations of interlayer.

FIGS. 7A and 7B show graphical plots of data showing uniaxial compressive loading using core-drilled samples of ATHP and various combinations of interlayer (eprouvette refers to test specimen, charge de compression refers to compressive force, and Temps refers to Time). These combinations are set forth in Table 1. These combinations also led to low strength values and inaccurate stress-strain curves.

TABLE 1

| | no. | interlayer | strength (without OFA) (MPa) |
|---|---|---|---|
| A | 1 | heavy card stock top and bottom | 3.2 |
| | 2 | heavy card stock top and bottom | 3.7 |
| | 3 | heavy card stock/aluminum top and bottom | 3.4 |

TABLE 1-continued

| | no. | interlayer | strength (without OFA) (MPa) |
|---|---|---|---|
| | 4 | heavy card stock/aluminum top and bottom | 3.6 |
| | 5 | Teflon ®/aluminum top and bottom | 3.4 |
| | 6 | Teflon ®/aluminum top and bottom | 3.5 |
| | 7 | Teflon ®/silicone top and bottom | 1.1 |
| | 8 | Teflon ®/silicone top and bottom | 1.2 |
| B | 1 | Teflon ® top and bottom | 3.6 |
| | 2 | Teflon ® top and bottom | 3.5 |
| | 3 | Teflon ®/silicone top and bottom | 2.4 |
| | 4 | Teflon ®/silicone top and bottom | 2.2 |

To overcome these inadequate strength test results and inaccurate stress-strain curves it was discovered that an intermediate layer of a highly soft material (hereinafter soft material) would (1) lower stress concentrations and (2) simultaneously allow lateral movement of the specimen sample to further avoid stress concentration and non-uniform axial loading, and (3) have similar lateral displacement of the soft material and the ceramic specimen sample material. Such a soft intermediate layer that can (1) lower stress concentrations and (3) have similar lateral displacement of the soft material and the ceramic specimen sample material can be, for example, provided by a mat material of nonwoven fibers, for example, as Viledon™ filter mats supplied by Freudenberg Filtration Technologies™. To allow lateral movement of the specimen sample to further avoid stress concentration and non-uniform axial loading as in (3), a Teflon® layer, for example, can be combined with the mat material of nonwoven fibers. Thus, an example combination was Teflon®/mat/Teflon® disposed at both load surfaces of the specimen between the specimen surface and the load platens.

Figure 8A:
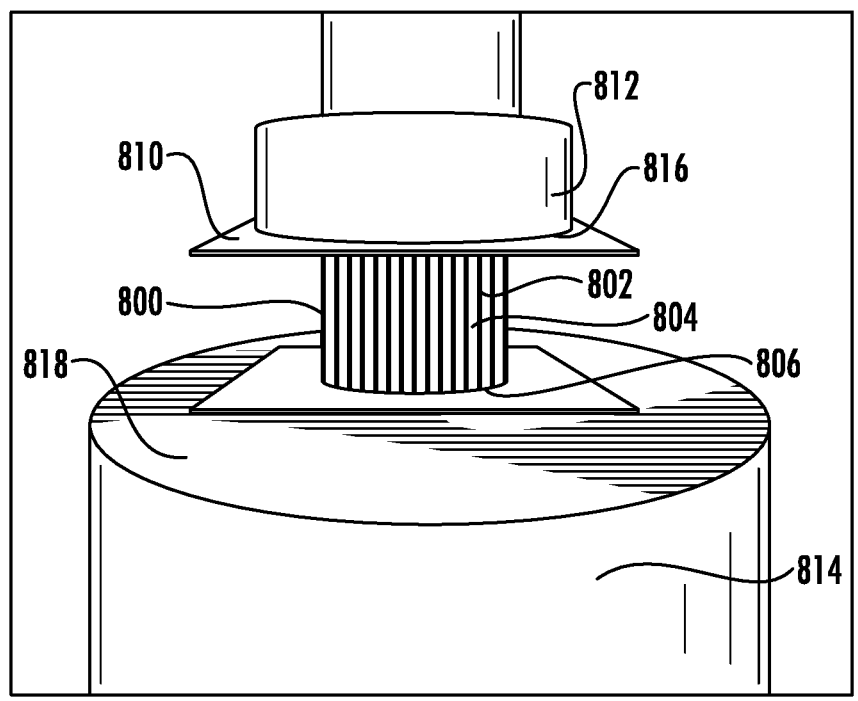
FIG. 8A shows a comparative mechanical apparatus set-up for compressive strength of a ceramic honeycomb body in an uniaxial A-axis test and FIG. 8B shows a mechanical apparatus set-up for compressive strength of a high porosity ceramic honeycomb body in an uniaxial A-axis test having an improved interlayer according to exemplary embodiments of the disclosure.

By using the mat as in an interlayer between the specimen sample and the platen fixture, the tested strength result increased significantly from a comparative layer (standard layer) to the improved layer. FIG. 8A shows a comparative mechanical apparatus set-up for compressive strength of a ceramic honeycomb body in an uniaxial A-axis test and FIG. 8B shows a mechanical apparatus set-up for compressive strength of a high porosity ceramic honeycomb body in an uniaxial A-axis test according to exemplary embodiments of the disclosure.

As shown in FIG. 8A, a porous ceramic honeycomb body 800 or other material specimen can be disposed in a test apparatus. The porous ceramic honeycomb body 800 illustrated in FIGS. 8A and 8B includes intersecting porous walls 802 defining channels 804 therebetween that extend axially from a first end face, such as a bottom end face 806, to a second end face, such as a top end face 808 (FIGS. 14A and 14B). The porous ceramic honeycomb body 800 outer peripheral surface extends from the top end face to the bottom end face and may support an after applied skin or a co-extruded skin. The mechanical testing apparatus includes a top platen 812 and a bottom platen 814. The top platen 812 has a bottom surface (load surface) 816 to exert a force on the top end face of the porous ceramic honeycomb body 800. The bottom platen 814 has a top surface (load surface) 818 to exert a force on the bottom end face 806 of the porous ceramic honeycomb body. The top and bottom platens 812, 814 apply a force to the specimen disposed between the bottom surface of the top platen 816 and the top surface of the bottom platen 818. A controller (not shown) can send a signal to control the platens and the forces applied to the specimen and receive data about the stress, strain, etc. of the specimen. The controller can further provide a result such as a stress strain curve of the strength test. In FIG. 8A a blotter paper 810, for example, a heavy card stock, is disposed between each end face of the porous ceramic honeycomb body 800 and the respective load surfaces of the platens 812, 814.

Figure 8B:
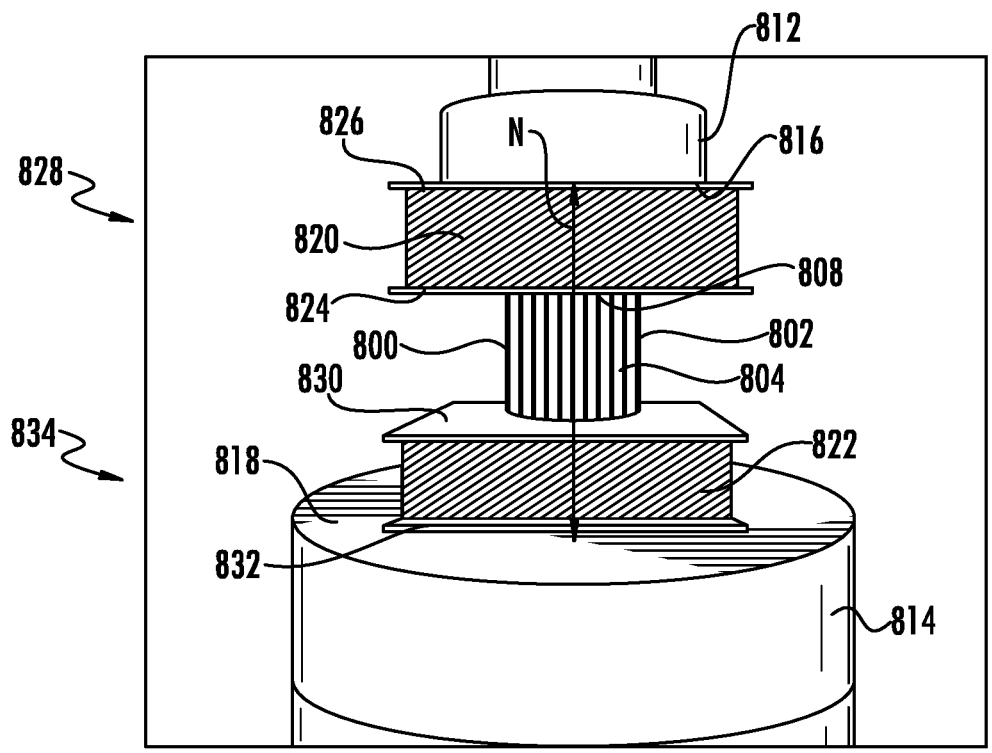

As shown in FIG. 8B, a porous ceramic honeycomb body 800 or other material specimen can be disposed in the test apparatus according to exemplary embodiments of the disclosure. The top and bottom platens 812, 814 are configured to apply a force to the specimen disposed between the bottom surface of the top platen 816 and the top surface of the bottom platen 818. In FIG. 8B an upper soft layer 820 of soft material, for example, a nonwoven fiber mat, is disposed between the top end face 808 of the porous ceramic honeycomb body 800 and the load surface 816 of the top platen 812. As mentioned, the upper soft layer 820 can be a layer of soft material or a combination of layers that provide a soft layer when combined. A lower soft layer 822, for example, a nonwoven fiber mat, can be disposed between the bottom end face 806 of the porous ceramic honeycomb body 800 and the load surface 818 of the bottom platen 814. Preferably, both the upper and lower soft layers 820, 822 are disposed between the respective end faces 808, 806 of the honeycomb body 800 and the load surfaces 816, 818 of the top and bottom platens 812, 814.

One or more additional layers can be disposed between the upper soft layer 820 and the porous ceramic honeycomb body 800. The additional layers can be referred to herein as a lower top layer 824. One or more additional layers can be disposed between the upper soft layer 820 and the top platen 812. These additional layers can be referred to herein as an upper top layer 826. The upper soft layer 820 and combination of additional layers 824 and 826 as described are referred to herein as the first interlayer 828. That is, the first interlayer 828 can comprise the upper soft layer 820 alone or the upper soft layer 820 and at least one of the lower top layer 824 and the upper top layer 826. The first interlayer 828 comprising more than one layer is referred to herein as a laminate.

The upper top layer 826 includes a facing surface configured to contact the bottom surface 816 of the top platen 812 and an opposite surface having the upper soft layer 820 disposed thereon. The lower top layer 824 disposed on the upper soft layer 820 includes a facing surface configured to contact the top end face 808 of the porous ceramic honeycomb body 800.

One or more additional layers can be disposed between the lower soft layer 822 and the porous ceramic honeycomb body 800. These additional layers can be referred to herein as an upper bottom layer 830. One or more additional layers 832 can be disposed between the lower soft layer 822 and the bottom platen 814 and be referred to herein as a lower bottom layer 832. The lower soft layer 822 and combination of additional layers 830 and 832 are referred to herein as the second interlayer 834. That is, the second interlayer 834 can comprise the lower soft layer 822 alone or the lower soft layer 822 and at least one of the upper bottom layer 830 and the lower bottom layer 832. The second interlayer 834 comprising more than one layer is referred to herein as a laminate.

The lower bottom layer 832 includes a facing surface configured to contact the top surface 818 of the bottom platen 814 and an opposite surface having the lower soft layer 822 disposed thereon. The upper bottom layer 830 disposed on the lower soft layer 822 includes a facing surface configured to contact the bottom end face 806 of the porous ceramic honeycomb body 800.

According to these exemplary embodiments, the facing surfaces of the upper top layer 826 and the lower bottom layer 832 have a smoothness to be slidably movable laterally relative to the respective facing surfaces 816, 818 of the top platen 812 or the bottom platen 814 when in contact therewith. The upper soft layer 820 has a softness greater than the lower top layer 824 and the upper top layer 826. The lower soft layer 822 has a softness greater than the upper bottom layer 830 and the lower bottom layer 832. Further, the facing surfaces of the lower top layer 824 and the upper bottom layer 830 have a smoothness to be slidably movable laterally relative to the respective load surfaces 806, 808 of the porous ceramic honeycomb body when in contact therewith. For example, the lower top layer 824, the upper top layer 826, the upper bottom layer 830, and the lower bottom layer 832, can comprise polytetrafluoroethylene (PTFE), and the upper soft layer 820 and the lower soft layer 822 can comprise nonwoven fiber mat.

While a first interlayer 828 and a second interlayer 834 are illustrated in FIG. 8B, the disclosure is not limited to both the first interlayer 828 and the second interlayer 834. That is, exemplary embodiments of the disclosure can include the first interlayer 828, the second interlayer 834, or preferably, both the first interlayer 828 and the second interlayer 834.

Comparative uniaxial A-axis strength results from a comparative mechanical apparatus set-up for compressive strength of a high porosity ceramic honeycomb body are presented in FIG. 9A. The comparative mechanical apparatus set-up for compressive strength of a high porosity ceramic honeycomb body is illustrated schematically in FIG. 8A. FIG. 9B shows improved interlayer A-axis strength results from a mechanical apparatus set-up for compressive strength of a high porosity ceramic honeycomb body according to exemplary embodiments of the disclosure. The mechanical apparatus set-up for compressive strength of a high porosity ceramic honeycomb body according to exemplary embodiments of the disclosure is illustrated schematically in FIG. 8B.

Table 2 provides results of A-axis testing of examples of ATLP and ATHP. Five samples (Ex 1, Ex 2, Ex 3, Ex 4, and Ex 5) of ATLP and ATHP were tested using the comparative apparatus and five samples of ATLP and ATHP were tested using the improved apparatus having the improved interlayer according to exemplary embodiments of the disclosure. As presented in Table 2, the tested strength increased significantly from the comparative to the improved interlayer. The ATLP was composed of aluminum-titanate, strontium-aluminosilicate (SAS) and alumina. The ATLP porosity was equal to about 45%. The ATHP was composed of aluminum-titanate, mullite and cordierite. The ATHP porosity was equal to about 60%.

TABLE 2

| | | Strength (bar) | | | | | | |
|---|---|---|---|---|---|---|---|---|
| | Interlayer | Ex 1 | Ex 2 | Ex 3 | Ex 4 | Ex 5 | Mean | Standard deviation |
| ATLP | Comparative | 94.0 | 97.5 | 97.2 | 85.8 | 86.8 | 92.3 | 5.0 |
| | Improved | 106.2 | 102.1 | 100.6 | 99.6 | 98.6 | 101.4 | 2.7 |
| ATHP | Comparative | 30.1 | 28.1 | 27.8 | 29.2 | 29.1 | 28.8 | 0.8 |
| | Improved | 49.2 | 49.0 | 47.9 | 50.7 | 47.0 | 48.7 | 1.3 |

The plugged strength was considered to be indicative of a filter's strength. The ATLP and ATHP samples tested with the improved interlayer exhibited strengths approaching the plugged strengths. The ATLP plugged strength was measured as 111 bar. The comparative strength was 92.3 bar and the improved strength was 101.4 bar. The ATHP plugged strength was measured as 51 bar. The comparative strength was 28.8 bar and the improved strength was 48.7 bar. As can be seen, the improvement is more significant for the high porosity ceramic honeycomb bodies where the webs are more susceptible to stress concentration than the low porosity ceramic honeycomb bodies.

According to exemplary embodiments of the disclosure, various mat materials having various thicknesses and surface weights were investigated for the soft layer of the interlayer. Table 3 sets forth examples of mat material and FIGS. 10A, 10B, and 10C present testing results of these samples. FIGS. 10A, 10B, and 10C present graphical plot of data showing the impact of mat properties in the interlayer on improved A-axis strength results for high porosity ceramic honeycomb bodies according to exemplary embodiments of the disclosure.

TABLE 3

| Mat ref | Thickness (mm) | Weight (g/mm$^2$) |
|---|---|---|
| P15/500 | 20 | 350 |
| P15/350 | 14 | 200 |
| P15/150 | 8 | 100 |
| PSB/290 | 20 | 300 |
| PSB/275 | 15 | 180 |
| PSB/145 | 10 | 120 |

As can be seen from Table 3 and FIGS. 10A, 10B, and 10C, the properties of the soft layer of the interlayer, such as surface weight and thickness, affect A-axis measured strength values. Thickness has a more pronounced impact on the resulting strength measurement; the thicker the mat, the higher the measured strength value result. For the surface weight materials investigated, it was found that the mat thickness of 10 mm and above improved the A-axis measured strength values. The surface weight was also found to have an impact on improved measured strength values although to a lesser extent than the mat thickness. In this case, it was found that the greater the surface weight, the greater the impact on improved measured strength values. Thus, a highly soft material interlayer improved measured strength values.

Comparative uniaxial A-axis strength results from a comparative mechanical apparatus set-up for compressive strength of a high porosity ceramic honeycomb body compared to improved interlayer A-axis strength results from a mechanical apparatus set-up for compressive strength of a high porosity ceramic honeycomb body according to exemplary embodiments of the disclosure are presented in FIG. 11. The samples of high porosity ceramic honeycomb bodies tested had a 300/8 geometry (300 cells per square inch and 8 mil wall thickness) and a porosity of 66%. These results demonstrate that the improved interlayer provides improved measured strength values for various types of high porosity cellular ceramic materials.

According to some of these exemplary embodiments a method of testing the high porosity ceramic honeycomb body 800 includes placing the high porosity ceramic honeycomb body 800 between facing surfaces 816, 818 of the first platen 812 and the second platen 814 with the first end face 808 disposed toward the first platen 812 and the second end face 806 disposed toward the second platen 814. The method includes placing at least one intermediate platen 828, 834 between at least one of the facing surface 816 of the first platen 812 and the first end face 808, and the facing surface 818 of the second platen 814 and the second end face 806. Here, the first platen 812 and the second platen 814 each have hardness greater than the at least one intermediate platen 828, 834. The method includes applying a force to the high porosity ceramic honeycomb body 800 between the first platen 812 and the second platen 814 via the facing surfaces of first platen 816 and the second platen 818 and monitoring a result of applying the force. Here, the at least one intermediate platen 828, 834 has a surface weight of about 350 g/m$^2$ and a thickness in a direction N between the facing surfaces of the first platen 816 and the second platen 818 of at least about 20 mm.

FIG. 12 shows an oedometric compression mechanical apparatus set-up for oedometric compressive strength of a high porosity ceramic honeycomb body which also showed improved strength results with the improved interlayer according to exemplary embodiments of the disclosure. The oedometric chamber 1004 restrains the high porosity ceramic honeycomb body and a pushrod 1008 transfers the load via an improved interlayer to the high porosity ceramic honeycomb body according to these exemplary embodiments. In the comparative oedometric compression testing, a blotter paper was used in place of the improved interlayer.

FIG. 13 presents graphical plot of data showing ATHP and ATLP uniaxial strength measurements approach the strength of the actual product under testing conditions according to these exemplary embodiments of the disclosure. The ATHP comparative oedometric strength was 35.4 bar and the improved oedometric strength was 49.9 bar, close to the ATHP plugged strength of 51 bar. The ATLP comparative oedometric strength was 92.1 bar and the improved oedometric strength was 108.6 bar, close to the ATLP plugged strength of 111 bar.

During production of high porosity ceramic honeycomb bodies, A-axis testing can be performed for quality assurance (QA). Vertical stamp testing as used herein refers to A-axis testing on a portion of the high porosity ceramic honeycomb body face. FIG. 14A is a schematic cross section of a mechanical apparatus set-up for compressive strength of a high porosity ceramic honeycomb body in an uniaxial A-axis test according to exemplary embodiments of the disclosure. FIG. 14B is a perspective view of the mechanical apparatus set-up for testing high porosity ceramic honeycomb bodies shown in FIG. 14A. The apparatus of FIGS. 14A and 14B can be used for quality assurance (QA) vertical stamp testing.

Referring to FIGS. 14A and 14B, a force F10 can be applied in an axial direction "A" to the porous ceramic honeycomb body 800 disposed between a top platen 1412 and a bottom platen 1414 having a first interlayer 1418 disposed between the top platen 1412 load surface 1422 and a top end face 808 of the porous ceramic honeycomb body 800 and a second interlayer 1424 disposed between the bottom platen 1414 load surface 1426 and a bottom end face 806 of the porous ceramic honeycomb body 800. The force F10 can be confined to a portion of the porous ceramic honeycomb body 800 by the size of the top platen load surface 1422 to provide a QA test. That is, when the area of the porous ceramic honeycomb body 800 top end face 808 is H1, the area of the top platen load surface 1422 can be H2 such that the portion of the porous ceramic honeycomb body 800 corresponding to the area H2 can be vertical stamp tested. For example, the ratio H2/H1 can be less than 1/5, for example, between 1/15 and 1/7, or even 1/11 and 1/9. For example, the ratio of H2/H1 can be less than 1/10. In these exemplary embodiments the area of the bottom platen load surface 1426 can be about the area of H1 or greater and the honeycomb body bottom end face 806 can have an area of about H1.

Vertical stamp testing is applied in an axial direction "A" of the honeycomb body 800 and for convenience is referred to herein as vertical stamp testing. Although described with the axis "A" disposed vertically, this orientation is not particularly limited, for example, the honeycomb body 800 can be disposed horizontally (the axis "A" disposed horizontally), then the first and second platens 1412, 1414 may exert a horizontal force to the end faces 806, 808 of the honeycomb body 800.

As shown in FIGS. 14A and 14B, the top platen 1412 can be disposed at position P1 to stamp test the porous ceramic honeycomb body 800. Position P1 can be at the center of the top end face 808 or spaced a distance R2 from the center of the top end face 808 in a direction "R". The facing surface 1422 of the top platen 1418 is configured to move in direction "A" offset from the center of the surface area of the bottom platen 1414. The position P1 can be spaced a distance R1 from the peripheral edge of the top end face 808 to avoid erroneous results from interactions with the porous ceramic honeycomb body 800 edge.

The area of the top platen H2 can be 2% to 90% of the area of the top end face H1. Further, the area of the top platen H2 can be 2% to 90% of the area of the bottom platen H3. Several positions P1, P2, P3 may be stamp tested to determine the quality assurance of a highly porous ceramic honeycomb body 800.

According to some of these exemplary embodiments the vertical stamp testing can be conducted on a ceramic honeycomb body comprising end plugs 1430. An end plugged ceramic honeycomb body 801 can be a filter or partial filter as described above. The end plugs provide a strengthening effect to the ceramic honeycomb body. The strengthening effect allows the vertical stamp testing to be performed without one or both of the intermediate layers 1418, 1424. Referring to FIGS. 15A and 15B, a force F10 can be applied in an axial direction "A" to the porous ceramic honeycomb body 801 disposed between a top platen 1412 and a bottom platen 1414 having no interlayer disposed between the top platen 1412 load surface 1422 and a top end face 808 of the porous ceramic honeycomb body 801 and no interlayer disposed between the bottom platen 1414 load surface 1426 and a bottom end face 806 of the porous ceramic honeycomb body 801. The force F10 can be confined to a portion of the porous ceramic honeycomb body 801 by the size of the top platen load surface 1422 to provide a QA test. That is, when the area of the porous ceramic honeycomb body 801 top end face 808 is H1, the area of the top platen load surface 1422 can be H2 such that the portion of the porous ceramic honeycomb body 801 corresponding to the area H2 can be stamp tested.

As shown in FIGS. 15A and 15B, the top platen 1412 can be disposed at position P1 to vertically stamp test the porous ceramic honeycomb body 801. Position P1 can be at the center of the top end face 808 or spaced a distance R2 from the center of the top end face 808 in a direction "R". The facing surface 1422 of the top platen 1418 is configured to move in direction "A" offset from the center of the surface area of the bottom platen 1414. The position P1 can be spaced a distance R1 from the peripheral edge of the top end face 808 to avoid erroneous results from interactions with the porous ceramic honeycomb body 801 edge.

The area of the top platen H2 can be 2% to 90% of the area of the top end face H1. Further, the area of the top platen H2 can be 2% to 90% of the area of the bottom platen H3. Several positions P1, P2, P3 may be vertically stamp tested without an interlayer to determine the quality assurance of a highly porous ceramic honeycomb body 801.

FIG. 16A presents a graphical plot of data showing mechanical strength of ATHP plugged honeycomb bodies tested in apparatus of FIGS. 15A and 15B. The local stamping assesses mechanical strength of the porous ceramic honeycomb body that mimics canning-induced stress. As shown in FIG. 16A the local stamping strength was approximately 60 bar. FIG. 16B presents a graphical plot of data showing proof testing results of ATHP plugged honeycomb bodies tested in apparatus of FIGS. 15A and 15B. The proof testing was to a proof load of 30 bar. The 30 bar local stamping did not give rise to any height variation in the porous ceramic honeycomb bodies where height refers to the axial distance between end faces because the testing was performed in a vertical orientation. Likewise, the canning operation did not induce any damage to the AT HP porous ceramic honeycomb bodies.

Advantages of the apparatus and methods of strength testing provided in accordance with the present disclosure include assessing in a simple and cost-effective manner the strength of high porosity materials by allowing a simple geometry, such as cylindrical or rectangular shape, and avoiding costly dumbbell geometry. In case of filters where plugs are used, advantages of the apparatus and methods of strength testing provided in accordance with the present disclosure allow reproducing the strengthening effect of plugs and predicting the strength of a final product from simple core drilled geometries. Furthermore, many samples can be obtained from one honeycomb body, for example, a filter, and the local strength properties of the honeycomb body can be assessed. That is, apparatus and methods of strength testing provided in accordance with the present disclosure provide manufacturing cost savings and efficiencies in product development and/or quality control.

Advantages of the local vertical stamping apparatus and methods of strength testing and proof testing provided in accordance with the present disclosure include assessing in a simple and cost-effective manner the strength of plugged ceramic honeycomb bodies with good reproducibility, little to no sample preparation, a greater margin between the acceptance value and the local stamping strength (safety margin). For example, the results for 90 local vertical stamping tests on 18 different AT HP filters are presented in FIG. 16C. The acceptance value is shown as 30 bar and the local vertical stamping strength was in a range of about 54 to 74 bar.

According to exemplary embodiments of the disclosure, a side stamping test of porous ceramic honeycomb bodies is provided and now described and referred to herein as a horizontal stamping test. The horizontal stamping test was discovered to determine localized isostatic strength of the porous ceramic honeycomb bodies.

Failure modes obtained from three-dimension (3D) isostatic strength test results of porous ceramic honeycomb bodies were classified according to three failure modes. FIGS. 17A, 17B, and 17C illustrate failure modes 1, 2, and 3, respectively, for honeycomb bodies in 3D isostatic strength tests. The first failure mode (failure mode 1) manifested as cracked skin or skin fissures 1702 of the honeycomb bodies 1700 and breakage 1704 adjacent to the matrix-to-skin interface, with no end face cracks. The matrix 1706 includes the intersecting axially extending walls 1708 shown in cross-section in FIG. 17A. The skin 1710 is disposed on the matrix 1706 at an outer periphery thereof. Failure mode 1 was observed on 15 sample porous ceramic honeycomb bodies in a range of 13.9 to 20.4 bar. The second failure mode (failure mode 2) manifested as a crushed filter or crushed periphery 1712 over skin and many rows of cells at the periphery of the porous ceramic honeycomb bodies 1700. Failure mode 2 was observed on 7 sample porous ceramic honeycomb bodies in a range of 20.7 to 27.2 bar. The third failure mode (failure mode 3) manifested as a broken filter having face cracks 1714 of the porous ceramic honeycomb bodies 1700 or the samples broken into multiple pieces with significant skin cracking and axial and/or radial cracks 1716. Failure mode 3 was observed on 12 sample porous ceramic honeycomb bodies in a range of 18.0 to 36.0 bar.

FIG. 18 is a graphical plot of data showing porous ceramic honeycomb body failure modes versus isostatic pressure indicating skin/web interface strength may drive isostatic strength. For example, when the acceptance value was about 17 bar, the samples that exhibited an isostatic strength below the acceptance value failed by failure mode 1. The failure mode of the horizontal stamping test was found to mimic the failure mode 1 in the 3D isostatic strength tests. Horizontal testing using a whole porous ceramic honeycomb body demonstrated that a load at the central region (spaced apart from the end faces) reproduced failure mode 1. The pressure to failure in the horizontal stamping was similar to the failure pressure in the 3D isostatic strength tests.

FIG. 19A is an isometric perspective view of a honeycomb filter in a horizontal stamping apparatus according to exemplary embodiments of the disclosure. FIG. 19B is a detail isometric perspective view of an upper platen in the horizontal stamping apparatus shown in FIG. 19A. FIG. 19C is a side view of the honeycomb filter in the horizontal stamping apparatus of FIG. 19A.

As shown in FIG. 19A, a porous ceramic honeycomb body 1800 or other material specimen can be disposed in the test apparatus 1802 according to exemplary embodiments of the disclosure. The honeycomb body 1800 having an axis "A" extending in a direction from one end face 1804 to the other 1806 can be disposed in the test apparatus 1802 with the axis extending horizontally. A first platen (top platen) 1808 and a second platen (bottom platen) 1810 are configured to apply a force "F20" to the specimen disposed between the bottom surface of the top platen 1812 and the top surface of the bottom platen 1814. In this way, the force F20 can be applied radially. Although described as the axis "A" disposed horizontally, this orientation is not particularly limited, for example, the honeycomb body 1800 can be disposed vertically (the axis "A" disposed vertically), then the first and second platens 1808, 1810 may exert a horizontal force to the side 1816 of the honeycomb body 1800. In FIG. 19B an upper platen 1808 is shown having the bottom surface 1812 contoured to press on the side surface 1816 of the porous ceramic honeycomb body 1800. The lower platen 1810 has an upper surface 1814 contoured to match the side 1816 of the porous ceramic honeycomb body 1800. The upper platen bottom surface 1812 and the bottom platen upper surface 1814 apply the force F20 at opposing sides of the porous ceramic honeycomb body 1800.

The force F20 can be confined to a portion of the porous ceramic honeycomb body 1800 by the size of the top platen load surface 1812 to provide a QA test. That is, when the length of the porous ceramic honeycomb body 1800 side from end face to end face 1804, 1806 is L1, the length of the top platen load surface 1812 can be L2, a fraction of L1 in the same direction as L1 and the top platen load surface 1812 can have a width in the L3 direction such that a localized portion of the porous ceramic honeycomb body 1800 side 1816 corresponding to the area of the top platen load surface 1812 can be stamp tested. The top platen load surface 1812 in the L3 direction can be curved to match the honeycomb body side surface 1816 and extend a few degrees. For example, when the honeycomb body side surface 1816 describes a cylinder, L3 can extend from about 0.1° to about 15°. In general, L2 and L3 are not particularly limited other than the top platen load surface 1812 area is less than the lower platen 1810 upper surface 1814 area. The lower platen 1810 upper surface 1814 can be referred to as the support area. The top platen load surface 1812 area is preferably less than about 10% of the side surface 1816 supported on the lower platen 1810 upper surface 1814. The side surface 1816 illustrated in the Figures is the outer peripheral surface of a skin disposed on the honeycomb body matrix of intersecting walls.

The force F20 can be confined to a portion of the porous ceramic honeycomb body 1800 by the size of the top platen load surface 1812 to provide a test result. For example, the ratio L2/L1 can be less than 1/5, for example, between 1/15 and 1/7, or even 1/11 and 1/9. For example, the ratio of L2/L1 can be less than 1/10. In these exemplary embodiments the area of the bottom platen load surface 1814 can be such that the bottom platen load surface 1814 is in contact with about 1/4 to 1/2 of the curvature of the honeycomb body side surface 1816 on the side opposing the top platen load surface 1812 and the bottom platen load surface 1814 can extend along the axial length of the honeycomb body 1800 side 1816 a distance L1. In this way, the area of the top platen load surface 1812 is a fraction of the area of the honeycomb body 1800 side 1816 opposing the bottom platen load surface 1814 and the portion of the honeycomb body 1800 side 1816 disposed in contact with the bottom platen load surface 1814.

The horizontal stamping test can assess the localized stiffness of the honeycomb body in various axial positions. FIG. 19C is a side view of the honeycomb filter in the horizontal stamping apparatus having the top platen load surface 1812 adjacent to an end face of the honeycomb filter 1800. In such a position, for example, the effect of end plugs on the isostatic strength of the honeycomb filter can be assessed.

The test apparatus 1802 can have a rotation plate 1820 to track the angle of the load F20 relative to the channel wall directions or other angular reference of the honeycomb body. For example, when the channel walls are disposed to form rectilinear channels, the side stamp strength at the 90° positions can be compared to the side stamp strength at the 45° positions or other positions. FIG. 20A illustrates an angular study to determine local stiffness by horizontal stamping according to exemplary embodiments of the disclosure. For example, when the channel walls are disposed to form rectilinear channels, a first set of walls may be orientated in the 0° to 180° position and a second set of walls may be orientated in the 90° to 270° position, as both read on the inside scale. The first and second sets of walls intersect to form the rectilinear channels. Likewise, when the channel walls are disposed to form hexagonal channels, a first set of walls may be orientated in the 0° to 180° position, a second set of walls may be orientated in the 60° to 240° position, and a third set of walls may be orientated in the 120° to 300° position, as read on the inside scale. The test angles may then be demarcated from the wall positions as indicated on the outside scale in FIG. 20A for the rectilinear channels. In general, the rectilinear channels may be square and of different cross section size, such as shown in FIGS. 17A and 17B.

FIG. 20B presents a graphical plot of data showing local honeycomb body filter stiffness for a square cell geometry quantified by horizontal stamping according to exemplary embodiments of the disclosure. The local honeycomb body filter stiffness for the square cell geometry is shown on a scale of concentric circles in bar/mm ranging from about 25 bar/mm to about 41 bar/mm. As illustrated by the plot, the stiffness was found to be in a range of about 36 bar/mm to 39 bar/mm at the 0°, 90°, 180°, and 270° orientations corresponding to the first and second sets of intersecting walls. These positions can be referred to for convenience as the 90's. The local filter stiffness was a maximum at the 90's. Between the 90's at 45°, 150°, 225°, and 315°, the local filter stiffness was found to be at minimums of between about 25 bar/mm to about 27 bar/mm. These minimums were found generally around the 45's, that is, at angles midway between the 90's. The horizontal stamping test assessed the local filter stiffness at angles between the 90's and the 45's and generally found values between the minimum and maximum. The local filter stiffness at the 135° position was about 27 bar/mm and the local filter stiffness at the 150° position was about 26 bar/mm. The lower local filter stiffness at the 150° position may indicate a non-uniformity in the honeycomb body structure at his position. Such a result can be used to adjust manufacturing processes, to determine whether the honeycomb body can withstand a subsequent canning process, and/or to determine whether the honeycomb body can meet in-service requirements.

FIG. 21 is a graphical plot of data showing horizontal stamping strength of a porous ceramic honeycomb filter 1800. Insert "S1" shows a cross section through a portion of the honeycomb filter 1800 matrix 1830 of axially extending intersecting walls 1832 and honeycomb body side surface 1816 as outer surface of skin 1834. The intersecting walls 1832 define a matrix 1830 of large channels 1836 and small channels 1838. Proof strength 2101 was indicated as between about 14 bar and 19 bar by the horizontal stamping test with compressive displacement of between about 0.6 mm and about 0.7 mm. Horizontal stamping strength results are shown for localized horizontal stamping conducted at 0°, 45°, 90°, 135°, 180°, 225°, 270°, and 315°.

Insert "S2" in FIG. 21 shows a cross section through a portion of the honeycomb filter 1800 at a higher failure strength 2103 induced by the horizontal stamping test. The local failure strength 2103 was indicated as between about 20 bar and 27 bar by the horizontal stamping test with compressive displacement of between about 0.76 mm and about 1.8 mm. Horizontal stamping strength results are shown for localized horizontal stamping conducted at 0°, 45°, 90°, 135°, 180°, 225°, 270°, and 315°. The horizontal stamping test induced a brittle failure. As shown in insert "S2" in FIG. 21, the horizontal stamping test induced failure mode 1 indicating an acceptable surrogate for isostatic strength testing, that is, the horizontal stamping test provides localized isostatic strength. The horizontal stamping test induced failure mode 1 is shown as breakage 2104 adjacent to the matrix-to-skin interface, with no end face cracks. A side-by-side comparison is shown in FIGS. 22A and 22B.

FIG. 22A illustrates mode 1 failure by isostatic strength testing of a porous ceramic honeycomb filter and FIG. 22B illustrates mode 1 failure produced by horizontal stamping according to exemplary embodiments of the disclosure indicative of the isostatic strength of the porous ceramic honeycomb filter. As described above, failure mode 1 manifests as cracked skin or skin fissures 1702 of the honeycomb body 1700 and breakage 1704 adjacent to the matrix-to-skin interface, with no end face cracks by isostatic strength testing. The horizontal stamping test also induced a brittle failure. Cracked skin or skin fissures 2108 in the horizontal stamping test was induced by the top platen 1808 having dimensions of L2 in the axial direction and L3 in the circumferential direction. The horizontal stamping test induced failure mode 1 is shown as breakage 2104 adjacent to the matrix-to-skin interface in FIG. 22B similar to the breakage 1704 in FIG. 22A for the 3D isostatic strength testing. The failure pressure was also similar between the 3D isostatic strength and the horizontal stamping test.

FIG. 23 is a graphical plot of data showing horizontal stamping strength variability from 0° to 45° for a square cell geometry of a porous ceramic honeycomb filter. The horizontal stamping test is able to locally assess the strength variability with angular orientation. The impact of angular orientation appeared to indicate a lower strength at the 15° and 30° orientations.

FIGS. 24A and 24B show that close to center, between end faces axially, local strength varies with stamping angle. The weakest zone was detected between 15° and 37.5°. 0° and 45° were used as geometrical references. Horizontal stamping tests were conducted at various angular positions as shown. FIG. 25 is a graphical plot of data showing horizontal stamping strength variability along the axial length for a square cell geometry of a porous ceramic honeycomb filter. testing was conducted at angular positions 0°, 30°, and 45° for each of the axial positions near the center between end faces, at the inlet extreme, and at the outlet extreme. The extremes (inlet end and outlet end) showed the lowest local strength results. Outliers may help to understand failure mechanisms of the honeycomb body.

According to some of these exemplary embodiments the horizontal stamping test can assess locally the strength and stiffness of honeycomb bodies under pressure. Accordingly, the horizontal stamping test can assess the strength driving parameters and provide manufacturing process improvements to increase isostatic strength. Further, the horizontal stamping test can assess local variability in strength at various angular and axial orientations, such as the impact of plugs, pre-existing defects in the matrix such as cell deformation and pre-skin peeling, and impact of induced controlled damages. According to some of these exemplary embodiments the horizontal stamping test and the vertical stamping test assess the strength of honeycomb bodies for both impact of design and defects, as well as the strength of driving parameters such as plug strengthening effects.

While terms such as, top, bottom, side, upper, lower, vertical, and horizontal are used, the disclosure is not so limited to these exemplary embodiments. Instead, spatially relative terms, such as "top", "bottom", "horizontal", "vertical", "side", "beneath", "below", "lower", "above", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

It will be understood that for the purposes of this disclosure, "at least one of X, Y, and Z" can be construed as X only, Y only, Z only, or any combination of two or more items X, Y, and Z (e.g., XYZ, XYY, YZ, ZZ).

"About" modifying, for example, the quantity of an ingredient in a composition, concentrations, volumes, process temperature, process time, yields, flow rates, pressures, viscosities, and like values, and ranges thereof, employed in describing the embodiments of the disclosure, refers to variation in the numerical quantity that can occur, for example: through typical measuring and handling procedures used for preparing materials, compositions, composites, concentrates, or use formulations; through inadvertent error in these procedures; through differences in the manufacture, source, or purity of starting materials or ingredients used to carry out the methods; and like considerations. The term "about" also encompasses amounts that differ due to aging of a composition or formulation with a particular initial concentration or mixture, and amounts that differ due to mixing or processing a composition or formulation with a particular initial concentration or mixture.

Reference throughout this specification to exemplary embodiments and similar language throughout this specification may, but do not necessarily, refer to the same embodiment. Furthermore, the described features, structures, or characteristics of the subject matter described herein with reference to an exemplary embodiment may be combined in any suitable manner in one or more exemplary embodiments.

It will be apparent to those skilled in the art that various modifications and variations can be made in the present disclosure without departing from the spirit or scope of the disclosure. Thus, it is intended that the appended claims cover the modifications and variations of this disclosure provided they come within the scope of the appended claims and their equivalents.

The invention claimed is:

1. A mechanical testing apparatus to test the mechanical strength of a specimen of material, the apparatus comprising:
a first platen and a second platen comprising facing surfaces configured to apply a force to the specimen of material when disposed between the facing surfaces of the first platen and the second platen;
at least one intermediate platen configured to be disposed between at least one of: (i) the facing surface of the first platen and the specimen of material, and (ii) the facing surface of the second platen and the specimen of material, wherein the first platen and the second platen comprise a hardness greater than a hardness of the at least one intermediate platen; and
a controller configured to monitor a result when force is applied to the specimen of material disposed between the first platen and the second platen,
wherein the at least one intermediate platen comprises a nonwoven fiber mat and comprises a thickness in a direction N between the facing surfaces of the first platen and the second platen in a range of from 10 mm to 30 mm.

2. The apparatus of claim 1, wherein the at least one intermediate platen comprises:
a first laminate comprising a facing surface configured to contact the facing surface of the first platen or the second platen, a second laminate disposed on an opposite surface of the facing surface of the first laminate, wherein the second laminate comprises the nonwoven fiber mat, and a third laminate disposed on the second laminate, wherein the third laminate comprises a facing surface configured to contact a load surface of the specimen of material when force is applied to the specimen of material disposed between the first platen and the second platen.

3. The apparatus of claim 2, wherein the facing surface of the first laminate comprises a smooth surface slidably movable laterally relative to the facing surface of the first platen or the second platen when in contact therewith, the second laminate comprises a softness of an unconstrained compressive modulus <50 MPa and failure deformation >10% in direction N, the second laminate comprising a softness greater than the first laminate and the second laminate, and the facing surface of the third laminate comprises a smooth surface slidably movable laterally relative to the load surface of the specimen of material when in contact therewith.

4. The apparatus of claim 2, wherein the first laminate and the third laminate comprise polytetrafluoroethylene (PTFE).

5. The apparatus of claim 1, wherein the at least one intermediate platen comprises first and second intermediate platens disposed on the facing surfaces of the first platen and the second platen, respectively.

6. The apparatus of claim 1, wherein the facing surface of the second platen has a surface area and the facing surface of the first platen has a surface area in a range of 2% to 90% of the surface area of the facing surface of the second platen.

7. The apparatus of claim 1, wherein a surface area of the second platen has a center and the facing surface of the first platen is configured to move in direction N offset from the center of the surface area of the second platen and in line with the center of the surface area of the second platen.

8. The apparatus of claim 1, wherein the at least one intermediate platen comprises a softness of an unconstrained compressive modulus <50 MPa and a failure deformation >10%.

9. The apparatus of claim 1, wherein the at least one intermediate platen comprises a thickness in direction N of between 10 mm and 30 mm.

10. The apparatus of claim 1, wherein the nonwoven fiber mat has a surface weight in a range of 150 g/m² to 550 g/m².

11. A method of testing a high porosity ceramic honeycomb body, the method comprising:

disposing a high porosity ceramic honeycomb body comprising channels defined by a plurality of intersecting porous walls that extend along the axis of the high porosity ceramic honeycomb body between a first end face and a second end face between facing surfaces of a first platen and a second platen, the first end face disposed toward the first platen and the second end face disposed toward the second platen;

disposing at least one intermediate platen between at least one of: (i) the facing surface of the first platen and the first end face, and (ii) the facing surface of the second platen and the second end face, wherein the first platen and the second platen comprise a hardness greater than a hardness of the at least one intermediate platen;

applying a force to the high porosity ceramic honeycomb body between the first platen and the second platen via the facing surfaces of first platen and the second platen; and monitoring a result of applying the force to the high porosity ceramic honeycomb body, wherein the at least one intermediate platen comprises a nonwoven fiber mat and comprises a thickness in a direction N between the facing surfaces of the first platen and the second platen in a range of from 10 mm to 30 mm.

12. The method of claim 11, wherein the at least one intermediate platen comprises:

a first laminate comprising a facing surface contacting the facing surface of the first platen or the second platen, a second laminate disposed on an opposite surface of the facing surface of the first laminate, wherein the second laminate comprises the nonwoven fiber mat, and a third laminate disposed on the second laminate, wherein the third laminate comprises a facing surface contacting a load surface of the high porosity ceramic honeycomb body when force is applied to the high porosity ceramic honeycomb body disposed between the first platen and the second platen, the load surface being the first end face corresponding to the first platen or the second end face corresponding to the second platen.

13. The method of claim 11, wherein the at least one intermediate platen comprises first and second intermediate platens disposed on the facing surfaces of the first platen and the second platen, respectively.

14. The method of claim 11, wherein the first end face has a surface area and the facing surface of the first platen has a surface area in a range of 2% to 90% of the surface area of the first end face.

15. The method of claim 11, wherein the second end face has a surface area, and the facing surface of the second platen has a surface area greater than or equal to the surface area of the second end face.

16. The method of claim 11, wherein a surface area of the second platen has a center, and applying the force comprises applying the force via the facing surfaces of first platen and the second platen, with the first platen offset from the center of the surface area of the second platen and in line with the center of the surface area of the second platen.

17. The method of claim 11, wherein the facing surface of the first platen applies a force over 2% to 90% of a surface area of the first end face.

18. The method of claim 11, wherein the first platen applies a force over a plurality of different surface area portions of a surface area of the first end face.

19. The method of claim 11, wherein the nonwoven fiber mat has a surface weight in a range of 150 g/m² to 550 g/m².

20. A mechanical testing apparatus to test the mechanical strength of a honeycomb body having intersecting walls of porous ceramic material extending axially from a first end face to a second end face, and having a curved side surface, the apparatus comprising:

a first platen and a second platen comprising facing surfaces configured to apply a force to the honeycomb body when disposed on the curved side surface between the facing surfaces of the first platen and the second platen;

a controller configured to monitor a result when force is applied to the honeycomb body disposed between the first platen and the second platen, wherein the first platen comprises a curved surface configured to conform to a first portion of the curved side surface and apply the force over a first area of the curved side surface of the honeycomb body, and the second platen comprises a curved surface configured to conform to a second portion of the curved side surface and apply the force over a second area of the curved side surface of the honeycomb body, with the second area opposing the first area, and
wherein the second area is less than one-tenth of the first area.

\* \* \* \* \*